US011254976B2

(12) United States Patent
Shen et al.

(10) Patent No.: US 11,254,976 B2
(45) Date of Patent: *Feb. 22, 2022

(54) KINETIC EXCLUSION AMPLIFICATION OF NUCLEIC ACID LIBRARIES

(71) Applicant: Illumina, Inc., San Diego, CA (US)

(72) Inventors: Min-Jui Richard Shen, Poway, CA (US); Jonathan Mark Boutell, Nr Saffron Walden (GB); Kathryn M. Stephens, Poway, CA (US); Mostafa Ronaghi, San Diego, CA (US); Kevin L. Gunderson, Encinitas, CA (US); Bala Murali Venkatesan, San Diego, CA (US); M. Shane Bowen, La Jolla, CA (US); Kandaswamy Vijayan, San Diego, CA (US)

(73) Assignee: Illumina, Inc., San Diego, CA (US)

(*) Notice: Subject to any disclaimer, the term of this patent is extended or adjusted under 35 U.S.C. 154(b) by 211 days.

This patent is subject to a terminal disclaimer.

(21) Appl. No.: 16/544,670

(22) Filed: Aug. 19, 2019

(65) Prior Publication Data

US 2020/0040386 A1 Feb. 6, 2020

Related U.S. Application Data

(63) Continuation of application No. 15/672,161, filed on Aug. 8, 2017, now Pat. No. 10,385,384, which is a continuation of application No. 14/879,932, filed on Oct. 9, 2015, now Pat. No. 9,758,816, which is a continuation of application No. 14/512,693, filed on Oct. 13, 2014, now Pat. No. 9,169,513, which is a continuation of application No. 13/783,043, filed on Mar. 1, 2013, now Pat. No. 8,895,249.

(60) Provisional application No. 61/715,478, filed on Oct. 18, 2012, provisional application No. 61/660,487, filed on Jun. 15, 2012.

(51) Int. Cl.
*C12Q 1/6848* (2018.01)
*C12Q 1/6844* (2018.01)
*C12Q 1/6874* (2018.01)
*B01J 19/00* (2006.01)

(52) U.S. Cl.
CPC ........ *C12Q 1/6848* (2013.01); *B01J 19/0046* (2013.01); *C12Q 1/6844* (2013.01); *C12Q 1/6874* (2013.01); *B01J 2219/00585* (2013.01); *B01J 2219/00587* (2013.01); *B01J 2219/00608* (2013.01); *B01J 2219/00621* (2013.01); *B01J 2219/00637* (2013.01); *B01J 2219/00653* (2013.01); *B01J 2219/00675* (2013.01); *B01J 2219/00722* (2013.01)

(58) Field of Classification Search
CPC .. C12Q 1/6848; C12Q 1/6844; C12Q 1/6874; B01J 19/0046; B01J 2219/00585; B01J 2219/00587; B01J 2219/00608; B01J 2219/00621; B01J 2219/00637; B01J 2219/00653; B01J 2219/00675; B01J 2219/00722
See application file for complete search history.

(56) References Cited

U.S. PATENT DOCUMENTS

| 169,513 A | 11/1876 | Boyle |
| 4,787,963 A | 11/1988 | MacConnell |
| 5,130,238 A | 7/1992 | Malek |
| 5,223,414 A | 6/1993 | Zarling et al. |
| 5,227,265 A | 7/1993 | DeBoer et al. |
| 5,234,566 A | 8/1993 | Osman et al. |
| 5,455,166 A | 10/1995 | Walker |
| 5,605,662 A | 2/1997 | Heller et al. |
| 5,641,658 A | 6/1997 | Adams et al. |
| 5,681,751 A | 10/1997 | Begg et al. |
| 5,728,532 A | 3/1998 | Ackley |
| 6,214,587 B1 | 4/2001 | Dattagupta |

(Continued)

FOREIGN PATENT DOCUMENTS

| CN | 101437954 A | 5/2009 |
| CN | 101449161 A | 6/2009 |

(Continued)

OTHER PUBLICATIONS

Beniley, et al., "Accurate whole human genome sequencing using reversible terminator chemistry", Nature, vol. 456, No. 7218, Nov. 6, 2008, 53-59.
Bleuit, et al., "Mediator proteins orchestrate enzyme-ssDNA assembly during T4 recombination-dependent DNA replication and repair", PNAS 98, 2001, 8298-8305.
Dean, et al., "Comprehensive human genome amplification using multiple displacement amplification", PNAS, 99, 2002, 5261-5266.
Dressman, et al., "Transforming single DNA molecules into fluorescent magnetic particles for detection and enumeration of genetic variations", PNAS, 100(15), 2003, 8817-8822.

(Continued)

*Primary Examiner* — David C Thomas
(74) *Attorney, Agent, or Firm* — Klarquist Sparkman, LLP

(57) ABSTRACT

A method including (a) providing an amplification reagent including an array of sites, and a solution having different target nucleic acids; and (b) reacting the amplification reagent to produce amplification sites each having a clonal population of amplicons from a target nucleic acid from the solution. The reacting can include simultaneously transporting the nucleic acids to the sites at an average transport rate, and amplifying the nucleic acids that transport to the sites at an average amplification rate, wherein the average amplification rate exceeds the average transport rate. The reacting can include producing a first amplicon from a nucleic acid that transports to each of the sites, and producing subsequent amplicons from the nucleic acid or from the first amplicon, wherein the average rate at which the subsequent amplicons are generated exceeds the average rate at which the first amplicon is generated.

20 Claims, 10 Drawing Sheets

(56) References Cited

U.S. PATENT DOCUMENTS

| | | |
|---|---|---|
| 6,699,693 B1 | 3/2004 | Marians et al. |
| 6,929,915 B2 | 8/2005 | Benkovic et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,785,790 B1 | 8/2010 | Church et al. |
| 8,017,339 B2 | 9/2011 | Piepenburg et al. |
| 8,062,850 B2 | 11/2011 | Piepenburg |
| 8,071,308 B2 | 12/2011 | Piepenburg et al. |
| 8,895,249 B2 | 11/2014 | Shen et al. |
| 9,169,513 B2 | 10/2015 | Shen et al. |
| 9,758,816 B2 | 9/2017 | Shen et al. |
| 10,385,384 B2 * | 8/2019 | Shen .......... B01J 19/0046 |
| 2002/0055100 A1 | 5/2002 | Kawashima et al. |
| 2003/0124594 A1 | 7/2003 | Church et al. |
| 2004/0002090 A1 | 1/2004 | Mayer et al. |
| 2004/0096853 A1 | 5/2004 | Mayer |
| 2005/0064460 A1 | 3/2005 | Holliger et al. |
| 2005/0130173 A1 | 6/2005 | Leamon et al. |
| 2007/0099208 A1 | 5/2007 | Drmanac et al. |
| 2007/0128624 A1 | 6/2007 | Gormley et al. |
| 2007/0178516 A1 | 8/2007 | Sosnowski et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2009/0032401 A1 | 2/2009 | Ronaghi et al. |
| 2010/0009872 A1 | 1/2010 | Eid et al. |
| 2010/0111768 A1 | 5/2010 | Banerjee et al. |
| 2011/0059865 A1 | 3/2011 | Smith et al. |
| 2012/0021918 A1 | 1/2012 | Bashir et al. |
| 2012/0083417 A1 | 4/2012 | Zhou et al. |
| 2012/0270305 A1 | 10/2012 | Reed et al. |
| 2012/0295262 A1 | 11/2012 | Ronaghi et al. |
| 2012/0316086 A1 | 12/2012 | Lin et al. |
| 2013/0116153 A1 | 5/2013 | Bowen et al. |
| 2013/0225421 A1 | 8/2013 | Li et al. |
| 2013/0344540 A1 | 12/2013 | Reed et al. |
| 2014/0079923 A1 | 3/2014 | George et al. |
| 2014/0080717 A1 * | 3/2014 | Li ............... C12Q 1/6846 506/2 |

FOREIGN PATENT DOCUMENTS

| | | |
|---|---|---|
| CN | 102212621 A | 10/2011 |
| JP | 2001525193 A | 12/2001 |
| JP | 2010142232 A | 7/2010 |
| WO | WO 1991/006678 | 5/1991 |
| WO | WO 1998/53296 | 11/1998 |
| WO | WO 1999/029711 A1 | 6/1999 |
| WO | WO 2000/46408 | 8/2000 |
| WO | WO 02/46456 | 6/2002 |
| WO | WO 2003/095664 A2 | 11/2003 |
| WO | WO 2004/018497 | 3/2004 |
| WO | WO 2005/010145 | 2/2005 |
| WO | WO 2007/103389 A2 | 9/2007 |
| WO | WO 2007/123744 | 11/2007 |
| WO | WO 2007/131135 A2 | 11/2007 |
| WO | WO 2008/093098 | 8/2008 |
| WO | WO 2010/075188 | 7/2010 |
| WO | WO 2011/008217 A1 | 1/2011 |
| WO | WO 2011/038241 | 3/2011 |
| WO | WO 2011/106368 | 9/2011 |
| WO | WO 2012/047889 | 4/2012 |
| WO | WO 2012/106072 | 8/2012 |
| WO | WO 2012/170936 | 12/2012 |

OTHER PUBLICATIONS

Fixe, et al., "Electric-field assisted immobilization and hybridization of DNA oligomers on thin-film microchips", Institute of Physics Publishing, Nanotechnology 16, (2005), 2061-2071.

Hsiao, et al., "Electric-Field-Directed Self-Assembly of Active Enzyme-Nanoparticle Structures", Journal of Biomedicine and Biotechnology, vol. 2012, Article ID 178487, Oct. 13, 2011, 9 pages.

Lage, Jose M. et al., "Whole genome analysis of genetic alterations in small DNA samples using hyperbranched strand displacement amplification and array-CGH", Genome Research, vol. 13., Issue 2, Feb., Feb. 1, 2003, 294-307.

Lizardi, "Mutation detection and single-molecule counting using isothermal rolling-circle amplification", Nature Genetics, vol. 19, 1998, 225-232.

Morrical, et al., "Amplification of snap-back DNA synthesis reactions by the uvsX recombinase of bacteriophage T4.", JBC 266, 1991, 14031-14038.

Rybenkov, et al., "Probability of DNA knotting and the effective diameter of the DNA double helix", PNAS 90, 1993, 5307-5311.

Sobel, et al., "Effects of Na+ on the persistence length and excluded volume of T7 bacteriophage DNA", Biopolymers, 31, 1991, 1559-1564.

Sosnowski, et al., "Active microelectronic array system for DNA hybridization, genotyping and pharmacogenomic applications", Psychiatric Genetics, vol. 12, No. 4, Dec. 1, 2002, 181-192.

Thornton, "High Rate Thick Film Growth", Ann. Rev. Mater. Sci., 7, 1977, 239-260.

Walker, et al., "Strand displacement amplification—an isothermal, in vitro DNA amplification technique", NAR, 20, 1992, 1691-1696.

Zimmerman, et al., "Estimation of macromolecule concentrations and excluded volume effects for the cytoplasm of *Escherichia coli*", J. Mal. Biol. 222, 1991,599-620.

Chung et al., "A Palmtop PCR System with a Disposable Polymer Chip Operated by the Thermosiphon Effect", *Lab Chip. 10.2*: 202-210, Jan. 2010.

Gallup and Ackermann, "The 'PREXCEL-Q Method' for qPCR," *Int J Biomed Sci. 4.4*: 273-293, Dec. 2008.

Niemz et al., "Point-of-Care Nucleic Acid Testing for Infectious Diseases," *Trends Biotechnol. 29.5*: 240-250, May 2011.

Rothberg and Leamon, "The Development and Impact of 454 Sequencing", *Nat Biotechnol. 26.10*: 1117-1124, Oct. 2008.

Salehi-Ashtiani et al., "Large-Scale RACE Approach for Proactive Experimental Definition of C. Elegans ORFeome," *Genome Res. 19.12*: 2334-2342, Dec. 2009.

Zhang and Xing, "Single-Molecule DNA Amplification and Analysis Using Microfluidics," *Chem Rev. 110.8*: 4910-4947, Aug. 2010.

* cited by examiner

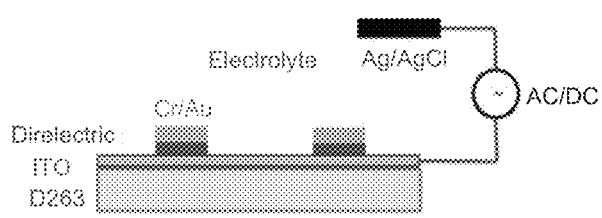 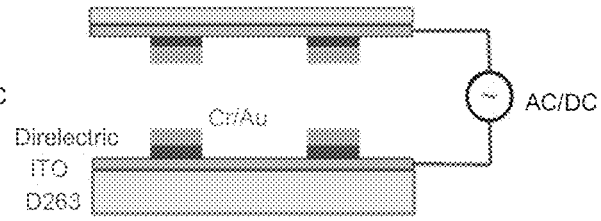
Figure 4A              Figure 4B
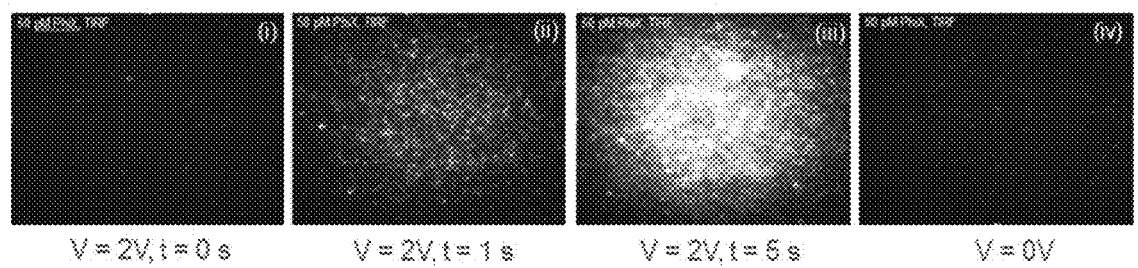
Figure 4C

KINETIC EXCLUSION AMPLIFICATION OF NUCLEIC ACID LIBRARIES

CROSS REFERENCE TO RELATED APPLICATIONS

This application is a continuation of U.S. patent application Ser. No. 15/672,161, filed Aug. 8, 2017, which is a continuation of U.S. patent application Ser. No. 14/879,932, filed Oct. 9, 2015, which is a continuation of U.S. patent application Ser. No. 14/512,693, filed Oct. 13, 2014, now issued as U.S. Pat. No. 9,169,513, which is continuation of U.S. patent application Ser. No. 13/783,043, filed Mar. 1, 2013, now issued as U.S. Pat. No. 8,895,249, which is based on, and claims the benefit of, U.S. Provisional Application No. 61/715,478, filed Oct. 18, 2012, and U.S. Provisional Application No. 61/660,487, filed Jun. 15, 2012. Each of the prior applications is incorporated by reference herein in its entirety.

BACKGROUND

This invention relates generally to molecular biology, and more specifically to nucleic acid synthesis and analysis.

Genetic analysis is taking on increasing importance in modern society. Genetic analyses have already proven useful for predicting a person's risk of contracting some diseases (diagnostics), determining the probability of therapeutic benefit vs. the risk of side effects for a person considering certain treatments (prognostics) and identifying missing persons, perpetrators of crimes, victims of crimes and casualties of war (forensics), to name a few. However, in many cases, appropriate genetic tests are not yet available or suffer from high error rates. One source for these problems is that many of the genetic tests currently used for diagnostics, prognostics and forensics rely on technologies that probe only a fraction of a person's genome. A person's genetic traits are encoded by a genome that contains over 3 billion base pairs and yet most genetic tests investigate mutations at only a few of these base pairs. By increasing the fraction of the genome probed, ideally up to and including all 3 billion base pairs in the genome, the accuracy of genetic tests can be improved and genetic tests can be developed for more diagnostic and prognostic situations.

A fundamental component of many genetic tests is the preparation of the genetic material that is to be tested. This is not a trivial matter when attempting to capture an entire genome and maintain its integrity. Two methods that are currently available for capturing large amounts of genetic material are emulsion polymerase chain reaction (ePCR) and cluster amplification (e.g. via bridge amplification). Their use in clinical and diagnostic applications is currently limited.

For ePCR, aqueous droplets are formed in an oil phase along with genome fragments and carrier beads. Conditions are chosen to optimize the probability that each droplet will isolate an individual genome fragment and a single carrier bead. The goal is for the droplets to form micro-reactors that prevent diffusion of genome fragments between droplets and hence between different beads. Several cycles of PCR amplification can then be carried out for the bulk emulsion such that in each droplet the bead is coated with clonal copies of the extant genome fragment. After amplification the beads are transferred to a detection substrate for evaluation in an analytical instrument. One complication with ePCR is that some of the beads end up in droplets without a genome fragment, thus producing blank beads. A bead enrichment step can be carried out to remove blank beads prior to use in the analytical instrument; however, this process is generally cumbersome and inefficient. Another complication with ePCR is that some droplets end up with more than one genome fragment, thus producing mixed-clone beads. Although mixed clone beads can often be identified and then ignored during analysis, their presence decreases the efficiency and in some cases the accuracy of the analysis.

Cluster amplification provides a more streamlined approach to capture and amplification of genetic material. In commercial embodiments, genome fragments are captured on a substrate surface to form "seeds" at random locations. After washing away excess genome fragments (i.e. those that have not been captured), several cycles of amplification are carried out to create clonal copies that form a cluster on the surface around each seed. Advantages of cluster amplification compared to ePCR include avoidance of the bead enrichment step, avoidance of the bead transfer step (from the emulsion to the detection substrate), and avoidance of messy, and often finicky, oil emulsions. However, a potential complication of commercial cluster amplification techniques is that they form a random pattern of clusters on the surface. Although, image registration protocols have been developed to locate and distinguish randomly located clusters, such protocols place an extra analysis burden on analytical devices. Furthermore, randomly located clusters tend to fill a surface less efficiently than theoretically possible for a spatially ordered pattern of clusters.

Thus, there exists a need for improved methods to prepare genetic material for diagnostic, prognostic and forensic analyses. The present disclosure addresses this need and provides other advantages as well.

BRIEF SUMMARY

The present disclosure provides a method for amplifying nucleic acids. The method can include the steps of (a) providing an amplification reagent including (i) an array of amplification sites, and (ii) a solution having a plurality of different target nucleic acids; and (b) reacting the amplification reagent to produce a plurality of amplification sites that each have a clonal population of amplicons from an individual target nucleic acid from the solution, wherein the reacting includes simultaneously (i) transporting the different target nucleic acids to the amplification sites at an average transport rate, and (ii) amplifying the target nucleic acids that are at the amplification sites at an average amplification rate, wherein the average amplification rate exceeds the average transportation rate. In particular embodiments, the number of the different target nucleic acids in the solution exceeds the number of amplification sites in the array. Typically, the different target nucleic acids have fluidic access to the plurality of amplification sites. Furthermore, each of the amplification sites can optionally have a capacity for several nucleic acids in the plurality of different nucleic acids.

Also provided is a method for amplifying nucleic acids that includes the steps of (a) providing an amplification reagent including (i) an array of amplification sites, and (ii) a solution having a plurality of different target nucleic acids; and (b) reacting the amplification reagent to produce a plurality of amplification sites that each include a clonal population of amplicons from an individual target nucleic acid from the solution, wherein the reacting includes (i) producing a first amplicon from an individual target nucleic acid at each of the amplification sites, and (ii) producing subsequent amplicons from the individual target nucleic acid at each of the amplification sites or from the first amplicon, wherein the average rate at which the subsequent amplicons are generated at the amplification sites exceeds the average rate at which the first amplicon is generated at the amplification sites. In particular embodiments, the number of the different target nucleic acids in the solution exceeds the number of amplification sites in the array. Typically, the different target nucleic acids have fluidic access to the plurality of amplification sites. Furthermore, each of the amplification sites can optionally have a capacity for several nucleic acids in the plurality of different nucleic acids.

The present disclosure further provides a method for amplifying nucleic acids that includes the steps of (a) providing an amplification reagent including (i) an array of amplification sites, and (ii) a solution having a plurality of different target nucleic acids; and (b) reacting the amplification reagent to produce a plurality of amplification sites that each have a clonal population of amplicons from an individual target nucleic acid from the solution, wherein the reacting includes simultaneously (i) capturing the different target nucleic acids at the amplification sites at an average capture rate, and (ii) amplifying the target nucleic acids captured at the amplification sites at an average amplification rate, wherein the average amplification rate exceeds the average capture rate.

Also provided is a method for amplifying nucleic acids that includes the steps of (a) providing an amplification reagent including (i) an array of amplification sites, and (ii) a solution having a plurality of different target nucleic acids; and (b) reacting the amplification reagent to produce a plurality of amplification sites that each include a clonal population of amplicons from an individual target nucleic acid from the solution, wherein the reacting includes (i) producing a first amplicon from an individual target nucleic acid that are captured at the amplification sites, and (ii) producing subsequent amplicons from the individual target nucleic acid that is captured at each of the amplification sites or from the first amplicon, wherein the average rate at which the subsequent amplicons are generated at the amplification sites exceeds the average rate at which the first amplicon is generated at the amplification sites.

Further provided is a method for creating a patterned surface of biomolecules, wherein the method can include the steps of (a) providing a reagent including (i) an array having non-contiguous features on a surface, the features being separated by interstitial regions of the surface, and (ii) a solution having a plurality of different target biomolecules; and (b) reacting the reagent to transport the biomolecules to the features and attach an individual biomolecule to each of the features, wherein an electric field is applied to the interstitial regions to repel the biomolecules from the interstitial regions.

BRIEF DESCRIPTION OF THE DRAWINGS

FIGS. 4A-4C show a flow cell architecture for electrochemical desorption of species from the flow cell surface. Electric potential can be applied across one conductive surface and the electrolyte as seen in FIG. 4A or across two conductive surfaces as shown in FIG. 4B. The flow cell configuration shown in FIG. 4B can also be used for field assisted pull down of DNA in real time achieving over a 100× concentration of DNA on the electrode surface in a few seconds as shown in FIG. 4C.

(FIG. 7A) Flow cell lane containing 2 μm Au dots; (FIG. 7B) lane containing 200 nm Au dots. Clusters are aligned over large areas to the micro and nanopatterned features, the spatially ordered nature of these clusters is confirmed by the corresponding Fourier Transforms (FFTs).

(FIG. 9B) median fluorescence intensity per flowcell lane following each step.

(FIG. 10B) spatially patterned clusters formed in the presence of a nucleic acid-repellant electric field at the interstitial regions and (FIG. 10C) randomly ordered clusters formed in the absence of the nucleic acid-repellant electric field at the interstitial regions.

DETAILED DESCRIPTION

Figure 1A:
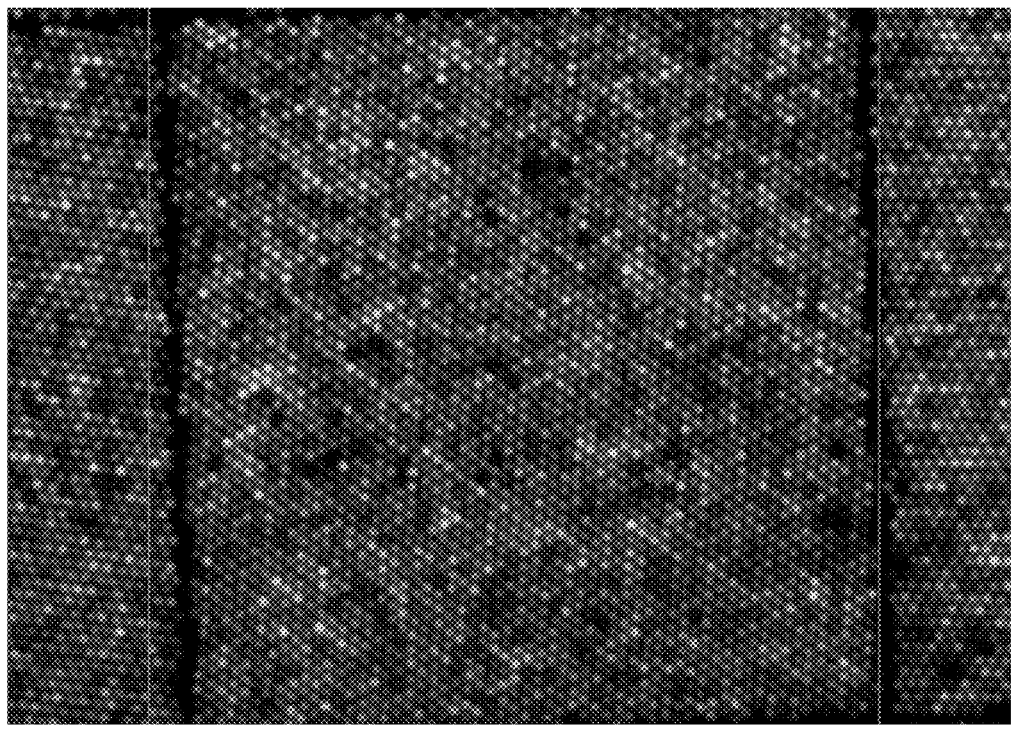
FIG. 1A shows a composite image (four color channels) obtained after a first sequencing cycle for a patterned flow cell produced by kinetic exclusion.

This disclosure provides nucleic acid libraries and methods for making nucleic acid libraries. In particular embodiments, a nucleic acid library of the present disclosure is in the form of an array of sites.

The array can have sites that are clonal with respect to particular nucleotide sequences. Accordingly, individual sites in the array can each have multiple copies of a single nucleotide sequence. For example, the sites can have clonal copies of a nucleic acid derived from a biological sample such as a genome or sub-fraction thereof (e.g. an exome), or a transcriptome (e.g. mRNA library or cDNA library) or sub-fraction thereof.

The fraction of sites in an array that are clonal can exceed the fraction predicted by the Poisson distribution. Thus an array produced by the methods set forth herein can have a super-Poisson distribution of clonal sites. The super-Poisson distribution can result during synthesis of the array and without the need for subsequent site enrichment or site purification steps (although enrichment and purification steps can be carried out if desired in at least some embodiments).

In some embodiments, the sites can be present as features on (or in) a substrate. In such embodiments, the features can be clonal, the fraction of features in an array that are clonal can exceed the Poisson distribution, and the features can be spatially arranged in a repeating pattern. Thus, the sites can be spatially ordered, for example, in a rectilinear grid, hexagonal grid or other desired pattern.

A nucleic acid library of the present disclosure can be made using a method that exploits kinetic exclusion. Kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification.

Kinetic exclusion can exploit a relatively slow rate for making a first copy of a target nucleic acid vs. a relatively rapid rate for making subsequent copies of the target nucleic acid or of the first copy. In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An advantage of arrays produced by methods set forth herein is that the clonal nature of the sites provides for accuracy in subsequent analysis. This avoids confounding results that would otherwise arise when detecting sites having mixed populations.

Another advantage of the arrays is that they have a super-Poisson distribution of clonal sites. This increases the complexity of the library by avoiding loss of genetic content that could otherwise occur due to sequestration into mixed sites.

A further advantage of the methods and arrays set forth herein is the provision of an array having features on a substrate, wherein the features are spatially arranged in a repeating pattern. As set forth above, the fraction of the features that are clonal can exceed the Poisson distribution. The Poisson distribution sets a maximum of 37% occupancy. In accordance with the methods set forth herein, the complement of features that are clonal can exceed 40%, 50%, 60%, 75% or more. Arrays produced by the methods set forth herein provide for more efficient filling of a substrate compared to random cluster arrays. Such arrays are also easier to evaluate analytically by avoiding complexities of image registration methods typically used for random cluster arrays.

Additionally, the methods set forth herein are advantageous for creating arrays on substrates that are patterned to facilitate detection. For example, several commercially available sequencing platforms rely on substrates having wells that provide a barrier to the diffusion of detection reagents (e.g. pyrophosphate in platforms available from 454 LifeSciences (a subsidiary of Roche, Basel Switzerland) or protons in platforms available from Ion Torrent (a subsidiary of Life Technologies, Carlsbad Calif.)) during sequence detection steps. The methods set forth herein can be advantageous for increasing the number of wells that are loaded with clonal populations as compared to standard cluster amplification methods that would be Poisson limited. The methods of the present disclosure are advantageous over ePCR methods as well by avoiding handling of emulsions and manipulations of beads.

Terms used herein will be understood to take on their ordinary meaning in the relevant art unless specified otherwise. Several terms used herein and their meanings are set forth below.

As used herein, the term "active seeding" refers to non-diffusive forces imposed on one or more nucleic acids to move the nucleic acid(s) toward or away from a location. The location can be an amplification site of an array. Non-diffusive forces can be provided by an external source such those that produce an electrical or magnetic fields, or an agent that imposes molecular crowding or chemical gradients within a reaction volume.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, the term "denaturation cycle" refers to a manipulation of a nucleic acid amplification reaction that changes the course of the amplification reaction such that complementary nucleic acid strands become separated from each other. Exemplary manipulations include, but are not limited to, introducing a chemical reagent that denatures nucleic acids, or physically altering the reaction, by heating or other manipulation, to denature nucleic acids. Several denaturation cycles can be included in a cyclic amplification reaction. Several other cycles can also be included such as cyclic manipulations to induce a primer to hybridize to a nucleic acid strand. One or more denaturation cycles or other cycles can be omitted in a method set forth herein. As such, an amplification reaction of the present disclosure can be carried out without cyclical manipulations in at least some embodiments.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other.

As used herein, the term "fluidic access," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic access can occur when there are no barriers that prevent the molecule from entering the site, contacting the site, separating from the site and/or exiting the site. However, fluidic access is understood to exist even if diffusion is retarded, reduced or altered so long as access is not absolutely prevented.

As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, 25%, 50%, 60%, 70%, 80%, 90% or 95% of its nucleotides hydrogen bonded to a complementary nucleotide.

As used herein, the term "each," when used in reference to a collection of items, is intended to identify an individual item in the collection but does not necessarily refer to every item in the collection unless the context clearly dictates otherwise.

As used herein, the term "excluded volume" refers to the volume of space occupied by a particular molecule to the exclusion of other such molecules.

As used herein, the term "extendible" or "extendible state," when used in reference to a nucleic acid such as a primer, means that the nucleic acid is competent for addition of a nucleotide (e.g. via polymerase catalysis) or addition of an oligonucleotide (e.g. via ligase catalysis). A nucleic acid that is "non-extendible" or in a "non-extendible state" is not so competent, for example, due to the presence of an extension blocking moiety or the absence of a 3' hydroxyl.

As used herein, the term "interstitial region" refers to an area in a substrate or on a surface that separates other areas of the substrate or surface. For example, an interstitial region can separate one feature of an array from another feature of the array. The two regions that are separated from each other can be discrete, lacking contact with each other. In another example, an interstitial region can separate a first portion of a feature from a second portion of a feature. The separation provided by an interstitial region can be partial or full separation. Interstitial regions will typically have a surface material that differs from the surface material of the features on the surface. For example, features of an array can have an amount or concentration of capture agents or primers that exceeds the amount or concentration present at the interstitial regions. In some embodiments the capture agents or primers may not be present at the interstitial regions.

As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, the term "rate," when used in reference to transport, amplification, capture or other chemical processes, is intended to be consistent with its meaning in chemical kinetics and biochemical kinetics. Rates for two processes can be compared with respect to maximum rates (e.g. at saturation), pre-steady state rates (e.g. prior to equilibrium), kinetic rate constants, or other measures known in the art. In particular embodiments, a rate for a particular process can be determined with respect to the total time for completion of the process. For example, an amplification rate can be determined with respect to the time taken for amplification to be complete. However, a rate for a particular process need not be determined with respect to the total time for completion of the process.

As used herein, the term "recombinase" is intended to be consistent with its use in the art and includes, for example, RecA protein, the T4 uvsX protein, any homologous protein or protein complex from any phyla, or functional variants thereof. Eukaryotic RecA homologues are generally named Rad51 after the first member of this group to be identified. Other non-homologous recombinases may be utilized in place of RecA, for example, RecT or RecO.

As used herein, the term "single stranded binding protein" is intended to refer to any protein having a function of binding to a single stranded nucleic acid, for example, to prevent premature annealing, to protect the single-stranded nucleic acid from nuclease digestion, to remove secondary structure from the nucleic acid, or to facilitate replication of the nucleic acid. The term is intended to include, but is not necessarily limited to, proteins that are formally identified as Single Stranded Binding proteins by the Nomenclature Committee of the International Union of Biochemistry and Molecular Biology (NC-IUBMB). Exemplary single stranded binding proteins include, but are not limited to *E. coli* SSB, T4 gp32, T7 gene 2.5 SSB, phage phi 29 SSB, any homologous protein or protein complex from any phyla, or functional variants thereof.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "universal sequence" refers to a region of sequence that is common to two or more nucleic acid molecules where the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus a universal capture nucleic acid or a universal primer includes a sequence that can hybridize specifically to a universal sequence. Target nucleic acid molecules may be modified to attach universal adapters, for example, at one or both ends of the different target sequences.

The present disclosure provides a method for amplifying nucleic acids. The method includes the steps of (a) providing an amplification reagent including (i) an array of amplification sites, and (ii) a solution having a plurality of different target nucleic acids; and (b) reacting the amplification reagent to produce a plurality of amplification sites that each have a clonal population of amplicons from an individual target nucleic acid from the solution, wherein the reacting includes simultaneously (i) transporting the different target nucleic acids to the amplification sites at an average transport rate, and (ii) amplifying the target nucleic acids at the amplification sites at an average amplification rate, wherein the average amplification rate exceeds the average transport rate. In particular embodiments, the number of the different target nucleic acids in the solution exceeds the number of amplification sites in the array. Typically, the different target nucleic acids have fluidic access to the plurality of amplification sites. Furthermore, each of the amplification sites can optionally have a capacity for several nucleic acids in the plurality of different nucleic acids.

Also provided is a method for amplifying nucleic acids that includes the steps of (a) providing an amplification reagent including (i) an array of amplification sites, and (ii) a solution having a plurality of different target nucleic acids; and (b) reacting the amplification reagent to produce a plurality of amplification sites that each include a clonal population of amplicons from an individual target nucleic acid from the solution, wherein the reacting includes (i) producing a first amplicon from an individual target nucleic acid at each of the amplification sites, and (ii) producing subsequent amplicons from the individual target nucleic acid at each of the amplification sites or from the first amplicon, wherein the average rate at which the subsequent amplicons are generated at the amplification sites exceeds the average rate at which the first amplicon is generated at the amplification sites. In particular embodiments, the number of the different target nucleic acids in the solution exceeds the number of amplification sites in the array. Typically, the different target nucleic acids have fluidic access to the plurality of amplification sites. Furthermore, each of the amplification sites can optionally have a capacity for several nucleic acids in the plurality of different nucleic acids.

An array of amplification sites used in a method set forth herein can be present as one or more substrates. Exemplary types of substrate materials that can be used for an array include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon. In particular embodiments, a substrate can be within or part of a vessel such as a well, tube, channel, cuvette, Petri plate, bottle or the like. A particularly useful vessel is a flow-cell, for example, as described in US 2010/0111768 A1 or Bentley et al., Nature 456:53-59 (2008), each of which is incorporated herein by reference. Exemplary flow-cells are those that are commercially available from Illumina, Inc. (San Diego, Calif.). Another particularly useful vessel is a well in a multiwell plate or microtiter plate.

In some embodiments, the sites of an array can be configured as features on a surface. The features can be present in any of a variety of desired formats. For example, the sites can be wells, pits, channels, ridges, raised regions, pegs, posts or the like. As set forth above, the sites can contain beads. However, in particular embodiments the sites need not contain a bead or particle. Exemplary sites include wells that are present in substrates used for commercial sequencing platforms sold by 454 LifeSciences (a subsidiary of Roche, Basel Switzerland) or Ion Torrent (a subsidiary of Life Technologies, Carlsbad Calif.). Other substrates having wells include, for example, etched fiber optics and other substrates described in U.S. Pat. Nos. 6,266,459; 6,355,431; 6,770,441; 6,859,570; 6,210,891; 6,258,568; 6,274,320; US 2009/0026082 A1; US 2009/0127589 A1; US 2010/0137143 A1; US 2010/0282617 A1 or PCT Publication No. WO 00/63437, each of which is incorporated herein by reference. In several cases the substrates are exemplified in these references for applications that use beads in the wells. The well-containing substrates can be used with or without beads in the methods or compositions of the present disclosure. In some embodiments, wells of a substrate can include gel material (with or without beads) as set forth in U.S. Prov. App. No 61/769,289, which is incorporated herein by reference.

The sites of an array can be metal features on a non-metallic surface such as glass, plastic or other materials exemplified above. A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977), which is incorporated herein by reference. Metal layer deposition techniques, such as those exemplified above, can be combined with photolithography techniques to create metal regions or patches on a surface. Exemplary methods for combining metal layer deposition techniques and photolithography techniques are provided in Examples I and II below and in U.S. Ser. No. 13/492,661, which is incorporated herein by reference.

An array of features can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, features of an array can each have an area that is larger than about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$. Alternatively or additionally, features of an array can each have an area that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$. Indeed, a region can have a size that is in a range between an upper and lower limit selected from those exemplified above.

For embodiments that include an array of features on a surface, the features can be discrete, being separated by interstitial regions. The size of the features and/or spacing between the regions can vary such that arrays can be high density, medium density or lower density. High density arrays are characterized as having regions separated by less than about 15 µm. Medium density arrays have regions separated by about 15 to 30 µm, while low density arrays have regions separated by greater than 30 µm. An array useful in the invention can have regions that are separated by less than 100 µm, 50 µm, 10 µm, 5 µm, 1 µm or 0.5 µm.

In particular embodiments, an array can include a collection of beads or other particles. The particles can be suspended in a solution or they can be located on the surface of a substrate. Examples of bead arrays in solution are those commercialized by Luminex (Austin, Tex.). Examples of arrays having beads located on a surface include those wherein beads are located in wells such as a BeadChip array (Illumina Inc., San Diego Calif.) or substrates used in sequencing platforms from 454 LifeSciences (a subsidiary of Roche, Basel Switzerland) or Ion Torrent (a subsidiary of Life Technologies, Carlsbad Calif.). Other arrays having beads located on a surface are described in U.S. Pat. Nos. 6,266,459; 6,355,431; 6,770,441; 6,859,570; 6,210,891;

6,258,568; 6,274,320; US 2009/0026082 A1; US 2009/0127589 A1; US 2010/0137143 A1; US 2010/0282617 A1 or PCT Publication No. WO 00/63437, each of which is incorporated herein by reference. Several of the above references describe methods for attaching target nucleic acids to beads prior to loading the beads in or on an array substrate. It will however, be understood that the beads can be made to include amplification primers and the beads can then be used to load an array, thereby forming amplification sites for use in a method set forth herein. As set forth previously herein, the substrates can be used without beads. For example, amplification primers can be attached directly to the wells or to gel material in wells. Thus, the references are illustrative of materials, compositions or apparatus that can be modified for use in the methods and compositions set forth herein.

Amplification sites of an array can include a plurality of capture agents capable of binding to target nucleic acids. Exemplary capture agents include receptors and/or ligands having a respective binding partner attached to the target nucleic acids, examples of which are set forth previously herein. A particularly useful capture agent is a capture nucleic acid that is complementary to a sequence of one or more target nucleic acids. For example, capture nucleic acids that are present at an amplification site can have a universal capture sequence that is complementary to a universal sequence that is present in an adapter sequence of each target nucleic acid. In some embodiments, the capture nucleic acid can also function as a primer for amplification of the target nucleic acid (whether or not it also contains a universal sequence).

In particular embodiments, a capture agent, such as a capture nucleic acid, can be attached to the amplification site. For example, the capture agent can be attached to the surface of a feature of an array. The attachment can be via an intermediate structure such as a bead, particle or gel. Attachment of capture nucleic acids to an array via a gel is shown in Example I below and further exemplified by flow cells available commercially from Illumina Inc. (San Diego, Calif.) or described in WO 2008/093098, which is incorporated herein by reference. Exemplary gels that can be used in the methods and apparatus set forth herein include, but are not limited to those having a colloidal structure, such as agarose; polymer mesh structure, such as gelatin; or crosslinked polymer structure, such as polyacrylamide, SFA (see, for example, US Pat. App. Pub. No. 2011/0059865 A1, which is incorporated herein by reference) or PAZAM (see, for example, U.S. Prov. Pat. App. Ser. No. 61/753,833, which is incorporated herein by reference). Attachment via a bead can be achieved as exemplified in the description and cited references set forth previously herein.

In some embodiments, the features on the surface of an array substrate are non-contiguous, being separated by interstitial regions of the surface. Interstitial regions that have a substantially lower quantity or concentration of capture agents, compared to the features of the array, are advantageous. Interstitial regions that lack capture agents are particularly advantageous. For example, a relatively small amount or absence of capture moieties at the interstitial regions favors localization of target nucleic acids, and subsequently generated clusters, to desired features. In particular embodiments, the features can be concave features in a surface (e.g. wells) and the features can contain a gel material. The gel-containing features can be separated from each other by interstitial regions on the surface where the gel is substantially absent or, if present the gel is substantially incapable of supporting localization of nucleic acids. Methods and compositions for making and using substrates having gel containing features, such as wells, are set forth in U.S. Prov. App. No 61/769,289, which is incorporated herein by reference.

Target nucleic acids used in a method or composition of the present disclosure can be composed of DNA, RNA or analogs thereof. The source of the target nucleic acids can be genomic DNA, messenger RNA, or other nucleic acids from native sources. In some cases the target nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof.

Exemplary biological samples from which target nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli*, *Staphylococci* or *Mycoplasma pneumoniae*; an archae; a virus such as Hepatitis C virus or human immunodeficiency virus; or a viroid. Target nucleic acids can be derived from a homogeneous culture or population of the above organisms or alternatively from a collection of several different organisms, for example, in a community or ecosystem.

Target nucleic acids need not be derived from natural sources and can instead be synthesized using known techniques. For example, gene expression probes or genotyping probes can be synthesized and used to create an array in the methods set forth herein.

In some embodiments, target nucleic acids can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid. For example, PCR amplification produces fragments having a size defined by the length of the fragment between the flanking primers used for amplification.

A population of target nucleic acids, or amplicons thereof, can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for population of target nucleic acids, or amplicons thereof, can be in a range between a maximum and minimum value set forth above. It will be understood that amplicons generated at an amplification site (or otherwise made or used herein) can have an average strand length that is in a range between an upper and lower limit selected from those exemplified above.

In some cases a population of target nucleic acids can be produced under conditions or otherwise configured to have a maximum length for its members. For example, the maximum length for the members that are used in one or more steps of a method set forth herein or that are present in a particular composition can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of target nucleic acids, or amplicons thereof, can be produced under conditions or otherwise configured to have a minimum length for its members. For example, the minimum length for the members that are used in one or more steps of a method set forth herein or that are present in a particular composition can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for target nucleic acids in a population can be in a range between a maximum and minimum value set forth above. It will be understood that amplicons generated at an amplification site (or otherwise made or used herein) can have maximum and/or minimum strand lengths in a range between the upper and lower limits exemplified above.

In particular embodiments, the target nucleic acids are sized relative to the area of the amplification sites, for example, to facilitate kinetic exclusion. For example, the area for each of the sites of an array can be greater than the diameter of the excluded volume of the target nucleic acids in order to achieve kinetic exclusion. Taking, for example, embodiments that utilize an array of features on a surface, the area for each of the features can be greater than the diameter of the excluded volume of the target nucleic acids that are transported to the amplification sites. The excluded volume for a target nucleic acid and its diameter can be determined, for example, from the length of the target nucleic acid. Methods for determining the excluded volume of nucleic acids and the diameter of the excluded volume are described, for example, in U.S. Pat. No. 7,785,790; Rybenkov et al., *Proc. Natl. Acad. Sci. U.S.A.* 90: 5307-5311 (1993); Zimmerman et al., *J. Mol. Biol.* 222:599-620 (1991); or Sobel et al., *Biopolymers* 31:1559-1564 (1991), each of which is incorporated herein by reference.

Amplification sites of an array can include a plurality of primers that are used to produce amplicons from a target nucleic acid. In some embodiments, the primers that are present at an amplification site can have a universal priming sequence that is complementary to a universal sequence that is present in an adapter sequence of each target nucleic acid. In particular embodiments, the plurality of primers can be attached to the amplification site. The primers can be attached to an amplification site as set forth above for capture nucleic acids.

As set forth previously herein, the features on the surface of an array substrate can be non-contiguous, being separated by interstitial regions of the surface. In particular embodiments, the interstitial regions will have a substantially lower quantity or concentration of primers, compared to the features of the array. Interstitial regions that lack primers are particularly advantageous. For example, a relatively small amount or absence of primers at the interstitial regions favors localization of amplicons to features on the surface of the array. This configuration creates a border for each array feature, thereby imparting the feature with a finite capacity for amplicons produced by amplification of a seeded target nucleic acid in methods set forth herein.

A method of the present disclosure can include a step of reacting an amplification reagent to produce a plurality of amplification sites that each includes a clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way excludes subsequent target nucleic acids from landing at the site, thereby producing a clonal population of amplicons at the site. Thus, it is desirable in some embodiments that the rate at which amplicons are generated to fill the capacity of amplification sites exceeds the rate at which the individual target nucleic acids are transported to the individual amplification sites respectively.

In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

As demonstrated by the above example, amplification sites in an array need not be entirely clonal in all embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons.

In particular embodiments, a method of the present disclosure is carried out to simultaneously (i) transport target nucleic acids to amplification sites at an average transport rate, and (ii) amplify the target nucleic acids that are at the amplification sites at an average amplification rate, wherein the average amplification rate exceeds the average transport rate. Accordingly, kinetic exclusion can be achieved in such embodiments by using a relatively slow rate of transport. For example, a sufficiently low concentration of target nucleic acids can be selected to achieve a desired average transport rate, lower concentrations resulting in slower average rates of transport. Alternatively or additionally, a high viscosity solution and/or presence of molecular crowding reagents in the solution can be used to reduce transport rates. Examples of useful molecular crowding reagents include, but are not limited to, polyethylene glycol (PEG), ficoll, dextran, or polyvinyl alcohol. Exemplary molecular crowding reagents and formulations are set forth in U.S. Pat. No. 7,399,590, which is incorporated herein by reference. Another factor that can be adjusted to achieve a desired transport rate is the average size of the target nucleic acids.

In some embodiments of the methods, target nucleic acids can be transported, for example by diffusion or other process, to amplification sites, prior to initiation of amplification. In this case, kinetic exclusion can be achieved by exploiting a relatively slow rate of creating a first amplicon compared to the rate at which subsequent amplicons are made. For example, different rates of amplicon formation can be achieved by using a first primer for first amplicon formation that is initially in a temporary non-extendible state and other primers for subsequent amplicon formation that are in an extendible state throughout the amplification reaction. As such, a delay in the conversion of the first primer to an extendible state will cause a delay in first amplicon formation, whereas subsequent amplicon formation experiences no such delay. In this way, the average rate at which the subsequent amplicons are generated at the amplification sites exceeds the average rate at which the first amplicon is generated at the amplification sites.

A more detailed example of kinetic exclusion via differential rates of amplicon formation follows. An amplification site can include three subpopulations of primers attached thereto. The first subpopulation of primers functions to capture a target nucleic acid (via a capture sequence) and as a primer for first amplicon formation. The first subpopulation of primers is reversibly blocked from extension, for example, via a dideoxy nucleotide at the 3' end. The second subpopulation of primers can have a P5 primer sequence and the third population of primers can have a P7 primer sequence. The primers of the first and second subpopulations do not include the dideoxy nucleotide and are therefore fully extension competent. Target nucleic acids can be constructed to include (from 5' to 3') a P7 primer binding sequence, one of several different target nucleotide sequences, a P5 primer binding sequence, and a capture sequence complement. Several different target nucleic acids can be hybridized to the first subpopulation of primers (via the capture sequences). The capture primers can then be converted to an extendible state, for example, by treatment with a polymerase under pyrophosphorolysis conditions (e.g. in the presence of excess pyrophosphate). Conditions can be used where, on average, only one of the capture primers will be converted to an extendible form during the time period in which subsequent amplicons are produced to fill the amplification site. Thus, although several potentially contaminating target nucleic acids may be present at an individual amplification site, kinetic exclusion will result in amplicon formation from only one of the target nucleic acids, thereby creating a clonal population of amplicons at the amplification site. For illustrative purposes this example has been described with respect to a single amplification site, but it will be understood that the reaction can involve target nucleic attachment and amplification at an array of amplification sites.

Any of a variety of temporarily non-extendible primers can be used in a method set forth herein along with respective techniques and reagents for converting those primers to an extendible state. The example above describes use of a dideoxy nucleotide that is removed by pyrophosphorolysis. Other non-extendible nucleotides can be present on a primer and removed by pyrophosphorolysis. Furthermore, dideoxy nucleotides or other non-extendible nucleotides can be removed via other known techniques including, for example, exonuclease activity of a polymerase or other appropriate enzyme. In other embodiments, a primer can include a reversible terminator such as those used in terminator-based sequencing-by-synthesis methods. Examples of reversible terminators and techniques for their removal are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Although the use of differentially active primers to cause different rates of first amplicon and subsequent amplicon formation has been exemplified above for an embodiment where target nucleic acids are present at amplification sites prior to amplification, the method can also be carried out under conditions wherein the target nucleic acids are transported (e.g. via diffusion) to the amplification sites as amplification is occurring. Thus, kinetic exclusion can exploit both a relatively slow transport rate and a relatively slow production of first amplicon relative to subsequent amplicon formation. Thus an amplification reaction set forth herein can be carried out such that target nucleic acids are transported from solution to amplification sites simultaneously with (i) the producing of a first amplicon, and (ii) the producing of the subsequent amplicons at other sites of the array. In particular embodiments, the average rate at which the subsequent amplicons are generated at the amplification sites can exceed the average rate at which the target nucleic acids are transported from the solution to the amplification sites. In some cases, a sufficient number of amplicons can be generated from a single target nucleic acid at an individual amplification site to fill the capacity of the respective amplification site. The rate at which amplicons are generated to fill the capacity of respective amplification sites can, for example, exceed the rate at which the individual target nucleic acids are transported from the solution to the amplification sites.

An amplification reagent that is used in a method set forth herein is preferably capable of rapidly making copies of target nucleic acids at amplification sites. Typically an amplification reagent used in a method of the present disclosure will include a polymerase and nucleotide triphosphates (NTPs). Any of a variety of polymerases known in the art can be used, but in some embodiments it may be preferable to use a polymerase that is exonuclease negative. The NTPs can be deoxyribonucleotide triphosphates (dNTPs) for embodiments where DNA copies are made. Typically the four native species, dATP, dTTP, dGTP and dCTP, will be present in a DNA amplification reagent; however, analogs can be used if desired. The NTPs can be ribonucleotide triphosphates (rNTPs) for embodiments where RNA copies are made. Typically the four native species, rATP, rUTP, rGTP and rCTP, will be present in a RNA amplification reagent; however, analogs can be used if desired.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, each of which is incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

The rate at which an amplification reaction occurs can be increased by increasing the concentration or amount of one or more of the active components of an amplification reaction. For example, the amount or concentration of polymerase, nucleotide triphosphates, primers, recombinase, helicase or SSB can be increased to increase the amplification rate. In some cases, the one or more active components of an amplification reaction that are increased in amount or concentration (or otherwise manipulated in a method set forth herein) are non-nucleic acid components of the amplification reaction.

Amplification rate can also be increased in a method set forth herein by adjusting the temperature. For example, the rate of amplification at one or more amplification sites can be increased by increasing the temperature at the site(s) up to a maximum temperature where reaction rate declines due to denaturation or other adverse events. Optimal or desired temperatures can be determined from known properties of the amplification components in use or empirically for a given amplification reaction mixture. Properties of primers used for amplification can also be adjusted to increase amplification rate. For example, the sequence and/or length of primers can be adjusted. Such adjustments can be made based on a priori predictions of primer melting temperature ($T_m$) or empirically.

Another option for increasing the rate of amplification at an amplification site is to increase the local concentration of one or more active components of the amplification reaction at the amplification site. The active components can include one or more non-nucleic acid components. In some embodiments, one or more active components of an amplification reaction can be attracted to an amplification site using electrical manipulations such as electrophoresis, isotachophoresis, direct pulsing of current or voltage or the like. Alternatively or additionally, one or more of the amplification components can include an affinity tag that recruits it to the amplification site. An affinity tag can be charged such that electrical manipulations will attract an appropriately tagged component to an amplification site. Non-charged affinity tags can be used as well. For example, any of a variety of ligands or receptors known in the art, such as those set forth herein as examples of capture agents, can be used as affinity tags for a component of an amplification reaction. As is the case for capture agents used for nucleic acids, an amplification site can include a binding partner for an affinity tag of an amplification component. Thus, the local concentration of the affinity tagged amplification component can be increased due to interaction with the appropriate partner at the amplification site. In particular embodiments where the amplification site is a surface of a substrate, a binding partner for an affinity tag can be attached to the surface.

Furthermore, magnetic or optical forces can be used to increase the local concentration of amplification reagents. In such cases, one or more amplification reagents can include a magnetic tag or optical tag that can be manipulated by such forces.

The rate at which an amplification reaction occurs can be increased by increasing the activity of one or more amplification reagent. For example, a cofactor that increases the extension rate of a polymerase can be added to a reaction where the polymerase is in use. In some embodiments, metal cofactors such as magnesium, zinc or manganese can be added to a polymerase reaction or betaine can be added.

In some embodiments of the methods set forth herein, it is desirable to use a population of target nucleic acids that is double stranded. It has been surprisingly observed that amplicon formation at an array of sites under kinetic exclusion conditions is efficient for double stranded target nucleic acids. For example, a plurality of amplification sites having clonal populations of amplicons can be more efficiently produced from double stranded target nucleic acids (compared to single stranded target nucleic acids at the same concentration) in the presence of recombinase and single stranded binding protein. Nevertheless, it will be understood that single stranded target nucleic acids can be used in some embodiments of the methods set forth herein.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution, for example, when the amplification sites are capable of containing amplicons in a volume having a desired capacity. Preferably, an amplification technique used under conditions of kinetic exclusion in a method of the present disclosure will be carried out on solid phase. For example, one or more primers used for amplification can be attached to a solid phase at the amplification site. In PCR embodiments, one or both of the primers used for amplification can be attached to a solid phase. Formats that utilize two species of primer attached to the surface are often referred to as bridge amplification because double stranded amplicons form a bridge-like structure between the two surface-attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. Solid-phase PCR amplification can also be carried out with one of the amplification primers attached to a solid support and the second primer in solution. An exemplary format that uses a combination of a surface attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. The above-exemplified PCR techniques can be modified for non-cyclic amplification (e.g. isothermal amplification) using components exemplified elsewhere herein for facilitating or increasing the rate of amplification. Accordingly, the above-exemplified PCR techniques can be used under kinetic exclusion conditions.

RCA techniques can be modified for use in a method of the present disclosure. Exemplary components that can be used in an RCA reaction and principles by which RCA produces amplicons are described, for example, in Lizardi et al., *Nat. Genet.* 19:225-232 (1998) and US 2007/0099208 A1, each of which is incorporated herein by reference. Primers used for RCA can be in solution or attached to a solid support surface at an amplification site. The RCA techniques exemplified in the above references can be modified in accordance with teaching herein, for example, to increase the rate of amplification to suit particular applications. Thus, RCA techniques can be used under kinetic exclusion conditions.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a solid support surface at an amplification site. The MDA techniques exemplified in the above references can be modified in accordance with teaching herein, for example, to increase the rate of amplification to suit particular applications. Accordingly, MDA techniques can be used under kinetic exclusion conditions.

In particular embodiments a combination of the above-exemplified amplification techniques can be used to make an array under kinetic exclusion conditions. For example, RCA and MDA can be used in a combination wherein RCA is used to generate a concatameric amplicon in solution (e.g. using solution-phase primers). The amplicon can then be used as a template for MDA using primers that are attached to a solid support surface at an amplification site. In this example, amplicons produced after the combined RCA and MDA steps will be attached to the surface of the amplification site.

As exemplified with respect to several of the embodiments above, a method of the present disclosure need not use a cyclical amplification technique. For example, amplification of target nucleic acids can be carried out at amplification sites absent a denaturation cycle. Exemplary denaturation cycles include introduction of chemical denaturants to an amplification reaction and/or increasing the temperature of an amplification reaction. Thus, amplifying of the target nucleic acids need not include a step of replacing the amplification solution with a chemical reagent that denatures the target nucleic acids and the amplicons. Similarly, amplifying of the target nucleic acids need not include heating the solution to a temperature that denatures the target nucleic acids and the amplicons. Accordingly, amplifying of target nucleic acids at amplification sites can be carried out isothermally for the duration of a method set forth herein. Indeed an amplification method set forth herein can occur without one or more cyclic manipulations that are carried out for some amplification techniques under standard conditions. Furthermore, in some standard solid phase amplification techniques a wash is carried out after target nucleic acids are loaded onto a substrate and before amplification is initiated. However, in embodiments of the present methods, a wash step need not be carried out between transport of target nucleic acids to reaction sites and amplification of the target nucleic acids at the amplification sites. Instead transport (e.g. via diffusion) and amplification are allowed to occur simultaneously to provide for kinetic exclusion.

In some embodiments it may be desirable to repeat an amplification cycle that occurs under kinetic exclusion conditions. Thus, although copies of a target nucleic acid can be made at an individual amplification site without cyclic manipulations, an array of amplification sites can be treated cyclically to increase the number of sites that contain amplicons after each cycle. In particular embodiments, the amplification conditions can be modified from one cycle to the next. For example, one or more of the conditions set forth above for altering the rate of transport or altering the rate of amplification can be adjusted between cycles. As such, the rate of transport can be increased from cycle to cycle, the rate of transport can be decreased from cycle to cycle, the rate of amplification can be increased from cycle to cycle, or the rate of amplification can be decreased from cycle to cycle.

A method set forth herein can be modified to use electric field (e-field) assisted transport of target nucleic acids to amplification sites of the array. For example, each amplification site of an array can be electrically coupled to a power source to produce an electric charge that attracts target nucleic acids. In one configuration, a positive charge at the amplification sites can attract nucleic acids via the negatively charged sugar-phosphate backbone. Exemplary methods and apparatus for using e-field assist to attract nucleic acids to sites of an array are described in US 2009/0032401 A1, which is incorporated herein by reference. E-field assist can be used in a method of the present disclosure, for example, under conditions where a plurality of different target nucleic acids is in solution such that the nucleic acid targets have fluidic access to the array of amplification sites during each amplification step. The charge at each amplification site can be adjusted to achieve kinetic exclusion. Additionally or alternatively to adjusting the charge, other conditions set forth herein for altering target nucleic acid transport rates or for altering amplification rates can be adjusted to achieve kinetic exclusion. Accordingly, the charge at amplification sites of an array can be adjusted to attract target nucleic acids while amplification simultaneously occurs at various amplification sites of the array, wherein the average amplification rate exceeds the average rate at which the target nucleic acids are transported (i.e. under e-field assisted transport) to the amplification sites.

In particular embodiments that utilize e-field assisted transport of target nucleic acids to amplification sites, the e-field can be consistently applied throughout the course of the amplification reaction. Alternatively, the e-field can be changed (e.g. increased or decreased) as the amplification reaction progresses and as amplification sites fill with amplicons. For example, increasing the e-field can provide the benefit of increasing the number of amplification sites that acquire a target nucleic acid (that is in turn amplified to produce a clonal population of amplicons at each of the sites). The rate at which the e-field is increased, and the amplitude range for the increase, can be selected to balance the increasing rate of target nucleic acid transport over time with the increasing number of amplification sites that have become effectively filled over that same period of time. Again, depending upon the application of the arrays produced by the method, effective filling may be the point at which the amplification sites have become filled to capacity with copies of a first target nucleic acid, thereby preventing amplification of any secondary target nucleic acids at that site. Alternatively, effective filling can be the point at which amplification of a secondary target nucleic acid at a particular amplification site would produce a sufficiently low fraction of contaminating amplicons to be considered negligible or otherwise acceptable for the desired use of the array.

Generally, e-field assist allows a further level of control over transport of target nucleic acids to one or more amplification sites of an array. Although the use of e-field assist has been exemplified above in the context of transporting target nucleic acids to an array of amplification sites simultaneously with amplification occurring at various sites of the array, in alternative embodiments e-field assist can be used to transport target nucleic acids to amplification sites prior to initiation of amplification at the sites. E-field assist can be used in a method or composition set forth herein to transport target biomolecules other than target nucleic acids to a site of interest such as to a feature of an array.

In particular embodiments, an e-field can be applied to all of the amplification sites of an array substantially uniformly. Thus, target nucleic acids that are in solution will have an equal probability of being transported to any given amplification site. In an alternative embodiment, an e-field can be applied to only a subset of the amplification sites that are present in an array. In this way, e-field assist can be used to selectively fill some sites over others. Furthermore, if desired, an attractive charge can be applied at a first subset of amplification sites in order to transport target nucleic acids to the first subset of sites and in the meantime a repellant charge can be applied to a second subset of amplification sites to inhibit target nucleic acids from being transported to those sites or to remove (e.g. via desorption or degradation) target nucleic acids from the second subset of sites. Similarly a repellant charge can be applied to interstitial regions of an array to inhibit target nucleic acids from being transported to the interstitial regions or to remove (e.g. via desorption or degradation) target nucleic acids from the interstitial regions as set forth in further detail below and in Example III.

In particular embodiments, interstitial regions of an array can be electrically coupled to a power source to produce an electric charge that inhibits binding of or removes target nucleic acids or other biomolecules. In one configuration, a negative charge at the interstitial regions can repel nucleic acids via the negatively charged sugar-phosphate backbone. Alternatively or additionally, the charge in the interstitial region can be used to create surface-localized pH changes that electrochemically damage nucleic acids and biomolecules.

E-field repulsion can be used in a method of the present disclosure, for example, under conditions where a plurality of different target nucleic acids is in solution such that the nucleic acid targets have fluidic access to the array of amplification sites during each amplification step. The charge at the interstitial regions of an array can be adjusted to repel nucleic acids (e.g. by removal or binding inhibition) while the nucleic acids are captured at the features of the array and, optionally, amplified at the features under kinetic exclusion conditions. Additionally or alternatively to adjusting the charge, other conditions set forth herein for altering target nucleic acid transport rates to features or for altering amplification rates can be adjusted to achieve kinetic exclusion. Accordingly, the charge at interstitial regions of an array can be adjusted to repel target nucleic acids while amplification simultaneously occurs at various amplification sites of the array, wherein the average amplification rate exceeds the average rate at which the target nucleic acids are transported to the amplification sites. Accordingly, electric field repulsion at interstitial regions can be used in combination with other methods set forth herein for transporting nucleic acids (or other biomolecules) to features of an array and achieving kinetic exclusion.

Electric field repulsion at interstitial regions using methods and apparatus set forth herein can provide an advantage of improving specific localization of nucleic acids (or other biomolecules) at the features instead of at interstitial regions. Such advantages can follow whether the repulsion works via a mechanism of charge repulsion to inhibit binding of nucleic acids or other biomolecules, via surface-localized electrochemical damage of nucleic acids and biomolecules or via other mechanisms. Electric field repulsion at interstitial regions can be used to improve specific localization of nucleic acids or other biomolecules to features of interest, particularly when the features of interest have a height taller than the reach of surface-localized electrochemical damage.

Some embodiments can utilize electric field assisted transport of nucleic acids (or other biomolecules) to the features of an array in combination with electric field assisted repulsion of the nucleic acids (or other biomolecules) from the interstitial regions of the array. The attractive electric field and repulsive electric field can be applied simultaneously to the array or the two fields can be applied separately. For example, the two fields can be applied separately such that the fields are applied in alternate repetitions (e.g. the attractive field can be applied to the features while the repulsive field is off, then the attractive field can be turned off while the repulsive field is applied to the interstitial regions and this sequence can be repeated one or more times).

An electric field can be applied across a region of an array and an electrolyte or it can be applied across the region of the array and a second surface. For example, FIG. 4A shows a configuration where an electric field can be applied across an interstitial region of an array and an electrolyte and FIG. 4B shows a configuration where an electric field can be applied across an interstitial region of an array and a second surface. Similar configurations can be used to apply attractive fields to features of an array. Furthermore, the electric fields, whether applied to a feature or interstitial region, can be created by application of an alternating current or a direct current to the appropriate region of the array.

Accordingly, the disclosure provides a method for creating a patterned surface of biomolecules, wherein the method can include the steps of (a) providing a reagent including (i) an array having non-contiguous features on a surface, the features being separated by interstitial regions of the surface, and (ii) a solution having a plurality of different target biomolecules; and (b) reacting the reagent to transport the biomolecules to the features and attach an individual biomolecule to each of the features, wherein an electric field is applied to the interstitial regions to repel the biomolecules from the interstitial regions. Particularly useful biomolecules for use in the method are nucleic acids. The nucleic acids can be amplified at the features in this method under kinetic exclusion conditions such as those that are set forth elsewhere herein. In some embodiments that use electric fields a substrate used for an array can include a layer of transparent electrical conductor. The layer of electrical conductor may be used as an electrode to connect an electrical source such as a battery or a signal generator. If desired, a feature of an array (e.g. an inner surfaces of a well in an array of wells) can contain an exposed or an insulated conductive layer, wherein a voltage across the conductive layers can be used to manipulate the force on a nucleic acid and/or amplification reagents to control the rate of transport to the site, capture at the site, removal from the site and/or amplification at the site. In particular embodiments, an electric field can be applied on the outer surfaces of a well such that the electric field that penetrates the vessel walls induces an electrical force on reagents within the vessel, providing a degree of control over the rates of transport, capture, removal and/or amplification.

An array of the present disclosure, for example, having been produced by a method set forth herein, can be used for any of a variety of applications. A particularly useful application is nucleic acid sequencing. One example is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different sites of an array set forth herein can be subjected to an SBS technique under conditions where events occurring for different templates can be distinguished due to their location in the array.

Flow cells provide a convenient format for housing an array that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid templates. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Sequencing-by-ligation reactions are also useful including, for example, those described in Shendure et al. Science 309:1728-1732 (2005); U.S. Pat. Nos. 5,599,675; and 5,750,341, each of which is incorporated herein by reference. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference. In both Sequencing-by-ligation and sequencing-by-hybridization procedures, target nucleic acids (or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons at the sites of the arrays that are used to detect protons.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

An advantage of the methods set forth herein is that they provide for rapid and efficient creation of arrays from any of a variety of nucleic acid libraries. Accordingly the present disclosure provides integrated systems capable of making an array using one or more of the methods set forth herein and further capable of detecting nucleic acids on the arrays using techniques known in the art such as those exemplified above. Thus, an integrated system of the present disclosure can include fluidic components capable of delivering amplification reagents to an array of amplification sites such as pumps, valves, reservoirs, fluidic lines and the like. A particularly useful fluidic component is a flow cell. A flow cell can be configured and/or used in an integrated system to create an array of the present disclosure and to detect the array. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating arrays of nucleic acids and also determining the sequence of the nucleic acids include, without limitation, the MiSeq platform (Illumina, Inc., San Diego, Calif.) and devices described in U.S. Ser. No. 13/273,666, which is incorporated herein by reference. Such devices can be modified to make arrays using kinetic exclusion in accordance with the guidance set forth herein.

A system capable of carrying out a method set forth herein need not be integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating an array under kinetic exclusion conditions. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

Several applications for arrays of the present disclosure have been exemplified above in the context of ensemble detection, wherein multiple amplicons present at each amplification site are detected together. In alternative embodiments, a single nucleic acid, whether a target nucleic acid or amplicon thereof, can be detected at each amplification site. For example, an amplification site can be configured to contain a single nucleic acid molecule having a target nucleotide sequence that is to be detected and a plurality of filler nucleic acids. In this example, the filler nucleic acids function to fill the capacity of the amplification site and they are not necessarily intended to be detected. The single molecule that is to be detected can be detected by a method that is capable of distinguishing the single molecule in the background of the filler nucleic acids. Any of a variety of single molecule detection techniques can be used including, for example, modifications of the ensemble detection techniques set forth above to detect the sites at increased gain or using more sensitive labels. Other examples of single molecule detection methods that can be used are set forth in US 2011/0312529 A1; U.S. Ser. No. 61/578,684; and U.S. Ser. No. 61/540,714, each of which is incorporated herein by reference.

An array useful for single molecule nucleic acid detection can be created using one or more of the methods set forth herein with the following modifications. A plurality of different target nucleic acids can be configured to include both a target nucleotide sequence that is to be detected and one or more filler nucleotide sequences that are to be amplified to create filler amplicons. The plurality of different target nucleic acids can be included in an amplification reagent, such as those set forth elsewhere herein, and reacted with an array of amplification sites under kinetic exclusion conditions such that the filler nucleotide sequence(s) fills the amplification sites. Exemplary configurations that can be used to allow the filler sequences to be amplified while prohibiting amplification of the target sequence include, for example, a single target molecule having a first region with filler sequences flanked by binding sites for amplification primers present at the amplification site and a second region having a target sequence outside of the flanked region. In another configuration, a target nucleic acid can include separate molecules or strands that carry the target sequence and filler sequence(s), respectively. The separate molecules or strands can be attached to a particle or formed as arms of a nucleic acid dendrimer or other branched structure.

In a particular embodiment, an array having amplification sites that each contain both filler sequences and a target sequence can be detected using a primer extension assay or sequencing-by-synthesis technique. In such cases, specific extension can be achieved at the target nucleotide sequence as opposed to at the large amount of filler sequence by use of appropriately placed primer binding sites. For example, binding sites for sequencing primers can be placed upstream of the target sequence and can be absent from any of the filler sequences. Alternatively or additionally, the target sequence can include one or more non-native nucleotide analogs that are not capable of hydrogen bonding to standard nucleotides. The non-native nucleotide(s) can be placed downstream of the primer binding site (e.g. in the target sequence or in a region intervening the target sequence and the primer biding site) and as such will prevent extension or sequencing-by-synthesis until an appropriate nucleotide partner (i.e. one capable of hydrogen bonding to the non-native analog(s) in the target sequence) is added. The nucleotide analogs isocytosine (isoC) and isoguanine (isoG) are particularly useful since they pair specifically with each other but not with other standard nucleotides used in most extension and sequencing-by-synthesis techniques. A further benefit of using isoC and/or isoG in a target sequence or upstream of the target sequence is to prevent unwanted amplification of the target sequence during amplification steps by omitting the respective partner from the nucleotide mixture used for amplification.

It will be understood that an array of the present disclosure, for example, having been produced by a method set forth herein, need not be used for a detection method. Rather, the array can be used to store a nucleic acid library. Accordingly, the array can be stored in a state that preserves the nucleic acids therein. For example, an array can be stored in a desiccated state, frozen state (e.g. in liquid nitrogen), or in a solution that is protective of nucleic acids. Alternatively or additionally, the array can be used to replicate a nucleic acid library. For example, an array can be used to create replicate amplicons from one or more of the sites on the array.

Several embodiments of the invention have been exemplified herein with regard to transporting target nucleic acids to amplification sites of an array and making copies of the captured target nucleic acids at the amplification sites. Similar methods can be used for non-nucleic acid target molecules. Thus, methods set forth herein can be used with other target molecules in place of the exemplified target nucleic acids. For example a method of the present disclosure can be carried out to transport individual target molecules from a population of different target molecules. Each target molecule can be transported to (and in some cases captured at) an individual site of an array to initiate a reaction at the site of capture. The reaction at each site can, for example, produce copies of the captured molecule or the reaction can alter the site to isolate or sequester the captured molecule. In either case, the end result can be sites of the array that are each pure with respect to the type of target molecule that is present from a population that contained different types of target molecules.

In particular embodiments that use target molecules other than nucleic acids, a library of different target molecules can be made using a method that exploits kinetic exclusion. For example a target molecule array can be made under conditions where sites of the array are randomly seeded with target molecules from a solution and copies of the target molecule are generated to fill each of the seeded sites to capacity. In accordance with the kinetic exclusion methods of the present disclosure, the seeding and copying processes can proceed simultaneously under conditions where the rate at which copies are made exceeds the seeding rate. As such, the relatively rapid rate at which copies are made at a site that has been seeded by a first target molecule will effectively exclude a second target molecule from seeding the site. In some cases, seeding of a target molecule will initiate a reaction that fills a site to capacity by a process other than copying of the target molecule. For example, the capture of a target molecule at a site can initiate a chain reaction that eventually renders the site incapable of capturing a second target molecule. The chain reaction can occur at a rate that exceeds the rate at which the target molecules are captured, thereby occurring under conditions of kinetic exclusion.

As exemplified for target nucleic acids, kinetic exclusion when applied to other target molecules can exploit a relatively slow rate for initiating a repetitive reaction (e.g. a chain reaction) at a site of an array vs. a relatively rapid rate for continuing the repetitive reaction once initiated. In the example of the previous paragraph, kinetic exclusion occurs due to the relatively slow rate of target molecule seeding (e.g. relatively slow diffusion) vs. the relatively rapid rate at which a reaction occurs, for example, to fill the site with copies of the target molecule seed. In another exemplary embodiment, kinetic exclusion can occur due to a delay in the formation of a first copy of a target molecule that has seeded a site (e.g. delayed or slow activation) vs. the relatively rapid rate at which subsequent copies are made to fill the site. In this example, an individual site may have been seeded with several different target molecules. However, first copy formation for any given target molecule can be activated randomly such that the average rate of first copy formation is relatively slow compared to the rate at which subsequent copies are generated. In this case, although an individual site may have been seeded with several different target molecules, kinetic exclusion will allow only one of those target molecules to be copied.

Accordingly, the present disclosure provides a method for making an array of molecules that can include the steps of (a) providing a reagent including (i) an array of sites, and (ii) a solution having a plurality of different target molecules, wherein the number of the target molecules in the solution exceeds the number of sites in the array, wherein the different target molecules have fluidic access to the plurality of sites, and wherein each of the sites comprises a capacity for several target molecules in the plurality of different target molecules; and (b) reacting the reagent to produce a plurality of sites that each have a single target molecule from the plurality or to produce a plurality of sites that each have a pure population of copies from an individual target molecule from the solution, wherein the reacting includes simultaneously (i) transporting the different molecules to the sites at an average transport rate, and (ii) initiating a reaction that fills the site to capacity at an average reaction rate, wherein the average reaction rate exceeds the average transport rate. In some embodiments, step (b) can instead be carried out by reacting the reagent to produce a plurality of sites that each have a single target molecule from the plurality or to produce a plurality of sites that each have a pure population of copies from an individual target molecule from the solution, wherein the reacting includes (i) initiating a repetitive reaction (e.g. a chain reaction) to form a product from the target molecule at each of the sites, and (ii) continuing the reaction at each of the sites to form subsequent products, wherein the average rate at which the reaction occurs at the sites exceeds the average rate at which the reaction is initiated at the sites.

In the non-nucleic acid embodiments above, the target molecule can be an initiator of a repetitive reaction that occurs at each site of the array. For example, the repetitive reaction can form a polymer that precludes other target molecules from occupying the site. Alternatively, the repetitive reaction can form one or more polymers that constitute molecular copies of a target molecule that was transported to the site.

The following examples are intended to illustrate but not limit the present invention.

Example I

Super-Poisson Formation of Cluster Arrays on Flow Cells

This example describes a method to achieve super-Poisson formation of a cluster array on a flow cell for an Illumina (San Diego, Calif.) sequencing platform. The method described here is a process to capture a library element (e.g. a genome fragment) on a feature and to simultaneously clonally amplify the library element. A key feature of the process in this example is to control the rate of capture vs. the rate of amplification and to do so in a homogenous process. Many prior processes developed for high density seeding of Illumina flow cells, separate the capture of the library element from the clonal amplification process. In this example, the capture event initiates a clonal amplification event on the feature.

A patterned flow cell is prepared as follows. Glass flow-cells (Illumina, Inc., San Diego, Calif.) are coated with gold patches using a lift-off approach. Briefly, a photoresist layer is evenly coated over the surface of the glass flow-cell and patches of the photoresist are removed by photolithography to expose patches of the glass surface. A layer of gold is then deposited on the surface to form a continuous thin film over the photoresist regions and glass patches. Gold can be deposited using e-beam evaporation or sputtering as set forth in Thornton, *Ann. Rev. Mater. Sci.* 7:239-60 (1977), which is incorporated herein by reference. The photoresist layer is then removed by Acetone lift off to leave gold patches that are circular in shape, having a diameter that is less than 1 micron, and being surrounded by interstitial regions of glass surface. The gold patterned flow-cell is then coated with silane-free acrylamide (SFA) as described in WO 2008/093098 (which is incorporated herein). P5 and P7 primers are grafted to the polymerized SFA via a nitrobenzyl UV cleavable moiety (Glenn Research, Sterling, Va.). The flow-cell is positioned on a UV (302 nm) light source such that the gold patches create a mask for primers attached over the patches while any primers attached over interstitial regions are cleaved due to UV light exposure. The P5 and P7 primers that remain at the gold patches are capable of supporting clonal amplification of libraries (P5/P7).

Library elements are produced as follows. A genomic DNA (gDNA) library is fragmented and forked adapters having primer binding sites that are complementary to the P5 and P7 primers are ligated to the gDNA fragments, according to Illumina commercial sample preparation protocols.

Super-Poisson cluster array formation is carried out as follows. A solution is prepared containing the library elements (in double stranded form) and TwistAmp Basic reagent (TwistDx, Cambridge UK). The TwistAmp Basic reagent contains an enzyme mixture that can support template dependent amplification on the surface (DNA polymerase, single stranded binding protein and recombinase). The concentration of the library elements in solution is controlled such that the rate of hybridization capture of a library element by any feature is much lower than the rate of clonal amplification and sufficient exhaustion of the oligos available on the feature to capture another library element.

Optimal or otherwise desired concentration of the library elements for the solution can be determined empirically by titration using the above super-Poisson cluster array formation protocol followed by a sequencing run on an Illumina Sequencing device (e.g. GenomeAnalyzer™, HiSeq™ or MiSeq™).

Example II

Characterization of Patterned Cluster Arrays Created Under Kinetic Exclusion Conditions This example demonstrates super Poisson loading of monoclonal clusters onto patterned features using kinetic exclusion conditions.

A patterned flow cell was prepared as follows. Glass flow-cells (Illumina, Inc., San Diego, Calif.) were coated with gold pads using a lift-off approach as described in U.S. Ser. No. 13/492,661, which is incorporated herein by reference. Briefly, a photoresist layer was evenly coated over the surface of the glass flow-cell and patches of the photoresist were removed by photolithography to expose patches of the glass surface. A layer of gold was then deposited on the surface to form a continuous thin film over the photoresist regions and glass patches. Gold was deposited using e-beam evaporation as set forth in Thornton, *Ann. Rev. Mater. Sci.* 7:239-60 (1977), which is incorporated herein by reference. The photoresist layer was then removed by Acetone lift off to leave a hexagonal pattern of gold pads, wherein each of the gold pads was circular in shape, had a diameter of 500 nm, and was surrounded by interstitial regions of glass surface. The gold patterned flow-cell was then coated with silane-free acrylamide (SFA) as described in WO 2008/093098 (which is incorporated herein). Primers were grafted to the polymerized SFA via a nitrobenzyl UV cleavable moiety (Glenn Research, Sterling, Va.). The flow-cell was positioned on a UV (302 nm) light source such that the gold pads created a mask for primers attached over the pads while any primers attached over interstitial regions were cleaved due to UV light exposure. Cleaved primers were washed away leaving primers attached over the gold pads.

Clusters were grown on the gold pads using the TwistAmp Basic kit (TwistDx, Cambridge UK) as follows. A double stranded PhiX DNA library was mixed at different concentrations in the TwistAmp Basic Rehydration buffer and magnesium acetate reagents. The concentrations of PhiX DNA tested were 72 pM, 144 pM, 432 pM and 864 pM. These concentrations were in excess of the typical range of 9-10 pM DNA used for standard seeding of Illumina flow cells. Also, the PhiX DNA was double stranded in contrast to standard seeding of Illumina flow cells where template DNA is in single stranded form. The PhiX DNA containing mixtures were used to rehydrate TwistAmp Basic freeze-dried pellets and then flushed into respective lanes of the patterned flow cell at 38° C. Incubation was continued for 1 hour at 38° C. before washing with HT2 wash buffer (Illumina, Inc., San Diego Calif.) and SyBr Green staining the clusters. Clusters were then processed for sequencing by LMX1 treatment for 30 minutes to linearize the DNA in the clusters, 0.1N NaOH denaturation and hybridization of sequencing primer. The flow cell was then sequenced for 26 cycles on an Illumina HiSeq® 2000.

Figure 1B:
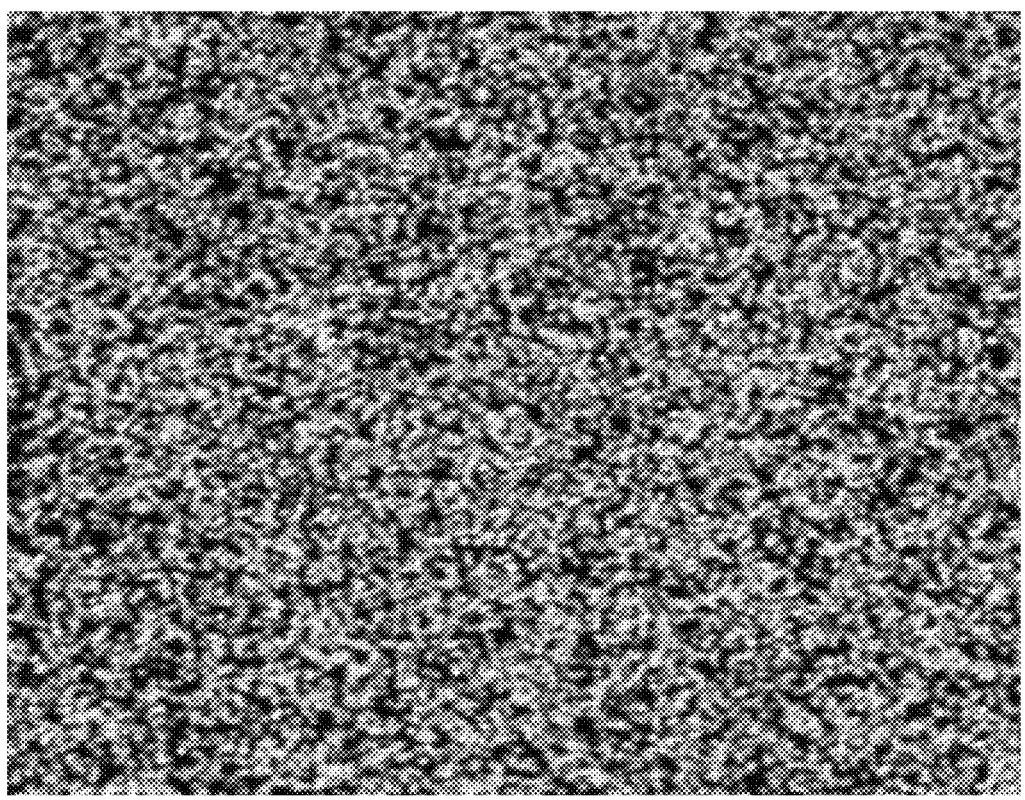
FIG. 1B shows a composite image (four color channels) obtained after a single sequencing cycle for a standard illumina flow cell having randomly located clusters.

Visual inspection of flow cell images showed that clusters were spatially ordered in a pattern corresponding to the pattern of gold pads on the surface. FIG. 1A shows a composite image for all four color channels obtained after a first sequencing cycle using a flow cell produced by the kinetic exclusion methods set forth above. For comparison, FIG. 1B shows a composite image obtained after a single sequencing cycle for a standard illumina flow cell having randomly located clusters.

Figure 2:
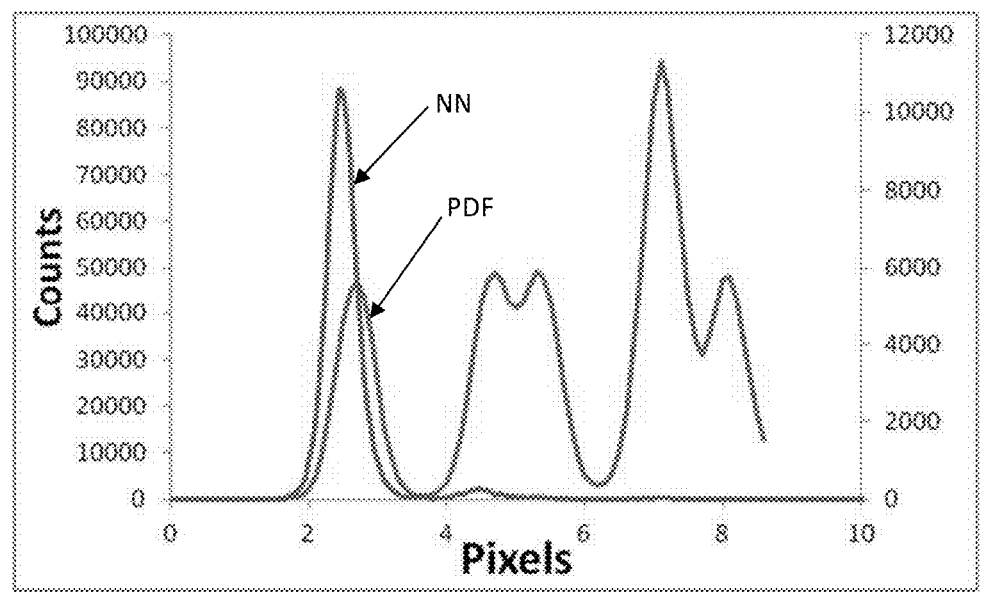
FIG. 2 shows PDF and NN functions for a composite image obtained after a first sequencing cycle using a patterned flow cell produced by kinetic exclusion.

Analysis of the pair distribution function (PDF) and nearest neighbor (NN) function for a composite image of the flow cell also indicated a high degree of order. Raw cluster density was calculated to be about 640,000 clusters per square millimeter for the image. The NN function was used to measure the average distance between nearest neighbor clusters in the image. As shown in FIG. 2, the NN function yielded predominantly a single peak around 2.3 pixels. This was consistent with the expected 1 micron pitch pattern for the pads, thereby suggesting a highly ordered array of clusters. Random clustering in contrast produces a much broader peak, with lower values approaching the detection limit of the cluster picking algorithm (1.2 pixels). The PDF in FIG. 2 is consistent with the expected structure for an ordered hexagonal array. For example, the PDF function showed an expected primary peak at 2.66 pixels and higher-order peaks corresponding to neighbors beyond the nearest were clearly visible and present at the expected peak ratios. Only a slight shift in peak location between the NN and PDF functions was observed. This low level of jitter indicated that that deviation from the theoretically perfect positions was quite low and well within acceptable levels.

Figure 3:
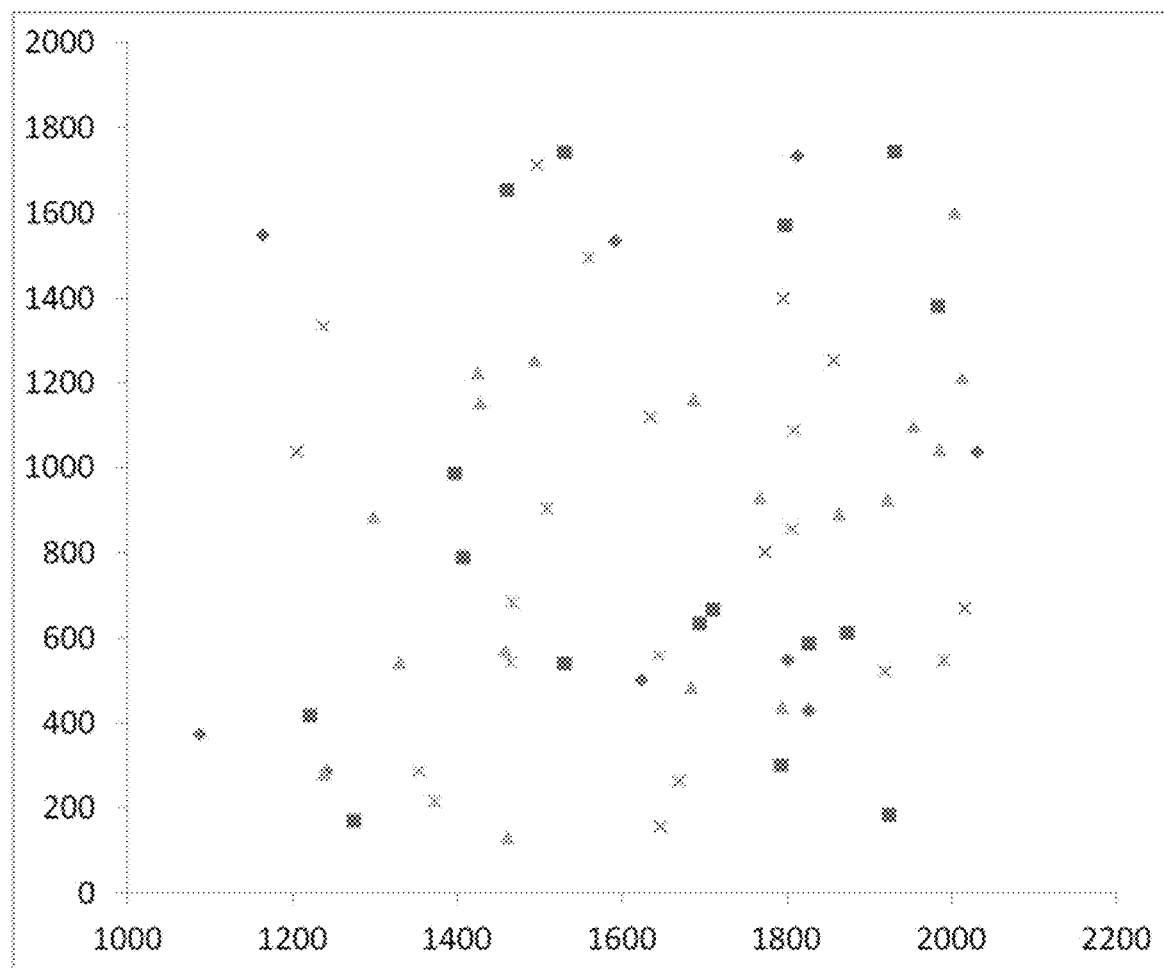
FIG. 3 shows a scatter plot of spatial positions of clusters that align to the first 5 genomic positions of PhiX genome. The different genomic positions are indicated by exes, asterisks, squares, triangles and diamonds.

Visual inspection of composite four color images also revealed an absence of undesirable pad hopping. 'Pad hopping' refers to the process of several adjacent pads being amplified from the same template sequence. Pad hopping is visually characterized in a four color image as contiguous patches of clusters that have the same color. The absence of same color patches for flow cells produced under kinetic exclusion conditions as set forth in this example indicated that undesirable levels of pad hopping did not occur. FIG. 3 provides a more quantitative representation of cluster color and spatial position indicating that pad hopping was not a problem. Specifically, FIG. 3 shows a scatter plot of spatial positions of clusters that align to the first 5 genomic positions of PhiX genome. The different genomic positions are indicated by exes, asterisks, squares, triangles and diamonds. The 5 symbol types are randomly distributed in the figure and do not clump which indicates that pad hopping was not a problem Sequence analysis for the 26 cycles of data was performed for the flow cells produced using kinetic exclusion conditions. The results indicated that 64% of the pads were occupied and 56% of the pads had clusters that were clonal. Thus, the methods produced a nearly 2 fold increase in clonal clusters over what is expected from Poisson loading, which would have predicted 36% of the pads being clonal if 64% of them were occupied. These results clearly showed super Poisson loading.

Example III

Active Electrical Desorption and Patterning of Biomolecules

This example demonstrates a method to spatially pattern biomolecules using electric fields. The methods described in this example rapidly seed DNA at target sites and electrochemically repel biomolecules from interstitial regions, resulting in highly patterned, addressable arrays of DNA clusters. The results shown here demonstrate the formation of flow cells having patterns of monoclonal nucleic acid clusters.

The method described in this example employs an electrical potential applied across one conductive surface and an electrolyte or across two conductive surfaces to actively desorb either physadsorbed or chemically conjugated molecules from one or both of the electrically biased surfaces. This active desorption method does not require any surface chemistry/surface modification, can desorb molecules very quickly (less than 5 minutes) and is less sensitive to process conditions than passive desorption methods. The conductive surfaces can be metallic (e.g. Titanium, Indium Tin Oxide) or semiconducting in nature and the applied potential can be AC or DC, resulting in an electrochemical reaction at the electrode/electrolyte interface. Applying an electric field improves the signal (at the sites of interest) to noise (from the interstitial regions) by an order of magnitude. The method described in this example can also be applied to planar electrodes for selective desorption, selective refunctionalization of electrodes and electrochemical patterning of species.

Flow Cell Architecture

The two architectures described above for the electrochemical desorption of biomolecules are illustrated in FIGS. 4A and 4B. Specifically, Indium Tin Oxide (ITO) was used as a conductive, transparent electrode material. ITO was deposited on a D263 surface via radio frequency sputtering. FIG. 4A shows the electrical potential applied across the conductive ITO layer and the electrolyte. FIG. 4B shows the potential applied across two parallel conductive ITO plates separated by a liquid medium. Both architectures can be used to electrically desorb species from the surface of the ITO. The gold (Au) nano-patterned sites are useful for targeted capture of thiolated biomolecules (e.g. thiolated avidin). The Au sites are separated from the underlying ITO using a dielectric spacer (e.g. $SiO_2$, SiN, diamond like carbon) to prevent electrochemistry on the Au.

The architecture in FIG. 4B can also be used to simultaneously rapidly concentrate DNA (e.g. by 100 fold) at the flow cell surface using electric fields as shown in the time lapse images of FIG. 4C. In these experiments, a potential (V) of 2V was applied across a 100 μm gap separating the two ITO surfaces. The increase in fluorescence over time, as observed using total internal reflection fluorescence (TIRF) imaging in FIG. 4C, is due to a large increase in the surface concentration of PhiX control DNA (labeled with YOYO dye) under an applied electric field at the top surface of the flow cell. Thus, the technique outlined here can be used to simultaneously electrochemically desorb biomolecules from the interstitial region whilst facilitating rapid seeding.

Experimental Workflow

Figure 5:
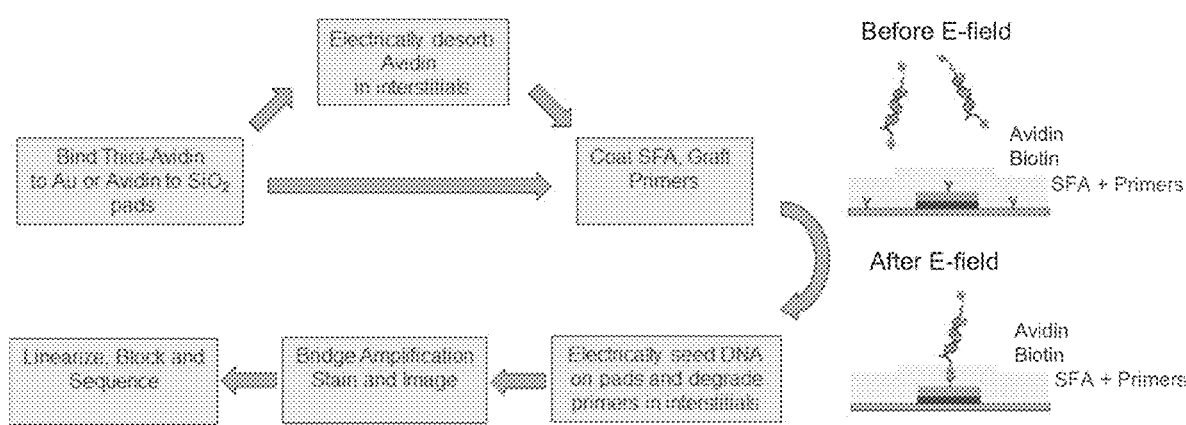
FIG. 5 shows an exemplary workflow for electric field assisted formation of biomolecule patterns.

The experimental workflow for active desorption experiments is outlined in FIG. 5. The method involves coating avidin on the surface of a flow cell, followed by coating with silane free acrylamide (SFA) and grafting primers to the SFA. SFA coating and grafting of P5 and P7 primers is carried out as described in WO 2008/093098 (which is incorporated herein). However, in the present methods, avidin is electrochemically patterned on Au or dielectric sites (separated by ITO interstitial regions) that are present on the flow cell surface using an electrical desorption step prior to SFA coating. Also, following P5 and P7 primer grafting, the electric field is applied to both rapidly seed the DNA on the Au or dielectric sites and to electrochemically desorb biomolecules (DNA, avidin, primers) from the ITO interstitials. Typically 2V is applied to effectively desorb molecules. Field durations of as little as 5 minutes can effectively desorb the majority of molecules in the interstitial regions. In addition, the results suggest that primer concentration in the interstitial region also decreases after electric field step. Cluster amplification is next performed as described in Bentley et al. *Nature* 456:53-59 (2008), followed by cluster staining using a dsDNA intercalating dye, then microscope imaging. The flow cell was then sequenced to determine cluster clonality using a HiSeq 2000 DNA sequencer (Illumina, Inc. San Diego). A schematic showing the effects of field assisted seeding and electrochemical desorption is shown in FIG. 5.

Experimental Results

Figure 6A:
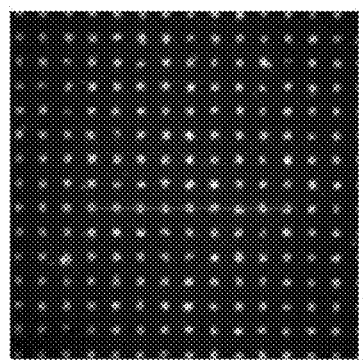
FIGS. 6A-6B show seeding of templates and cluster amplification of the templates on 2 μm Au features on an ITO background in the presence of an electric field (FIG. 6A), and with no electric field (FIG. 6B). Line profiles show fluorescence intensity across the labeled regions.
Figure 6A:
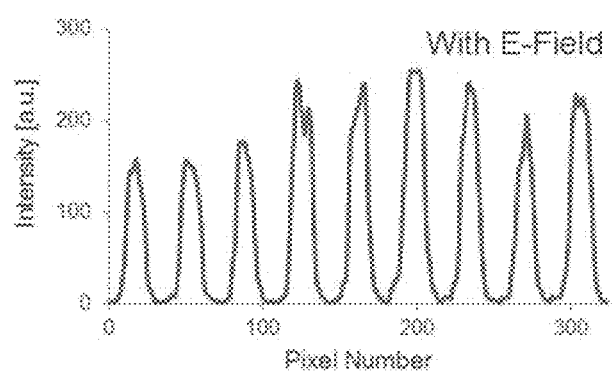
Figure 6B:
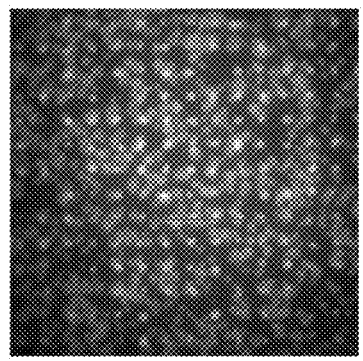
Figure 6B:
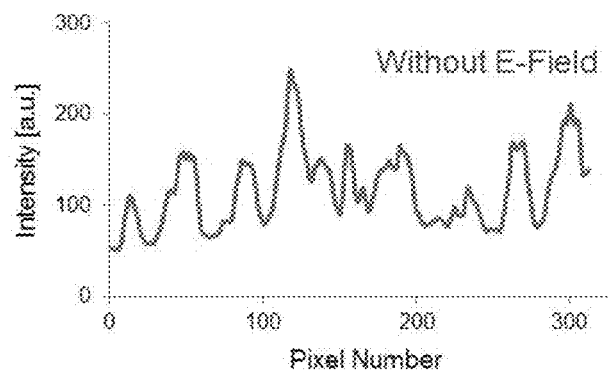

FIGS. 6A-6B illustrate results achieved using the flow cell architecture from FIG. 3, both with electric field (FIG. 6A) and without electric field (FIG. 6B). In the presence of the electric field, clusters are highly confined to the 2 μm Au sites with very little fluorescence observed in the interstitial areas. In the 2 μm sites, clusters are highly polyclonal due to the large size of the Au pad. The degree of polyclonality can be decreased by decreasing pad size to inhibit multiple templates from seeding via steric exclusion or polyclonality can be deceased using kinetic exclusion conditions. Also note, pixel intensity in the interstitial regions is close to 0 (line profile of FIG. 6A). In contrast, clusters are present on both the Au and the interstitial ITO surfaces in the absence of the electric field. The periodic pattern observed in the line profile of FIG. 6A is not observed in the line profile of FIG. 6B, confirming that the cluster confinement is the result of the electric field.

Figure 7A:
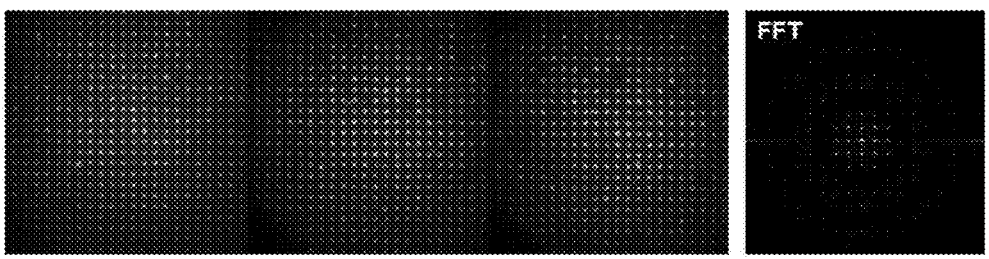
FIGS. 7A-7B show large area fluorescence images following seeding and clustering in the presence of an electric field.
Figure 7B:
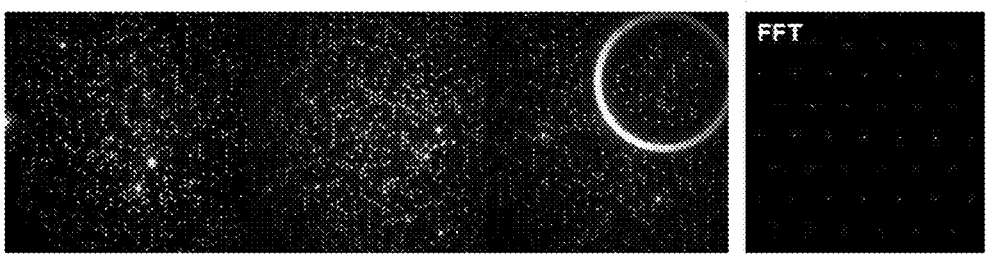
Figure 8:
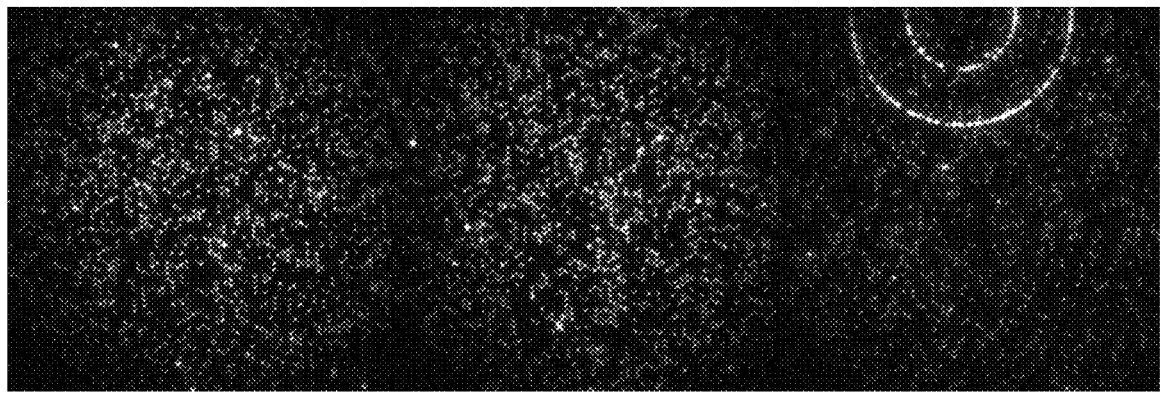
FIG. 8 shows DNA cluster formation on 700 nm diameter $SiO_2$ sites in the presence of electric field. Clusters are highly ordered with little fluorescence from interstitial areas.

The electronic field technique can be used to spatially pattern clusters on both micron sized sites as well as nano-patterned sites over large areas. Large area images of the patterned clusters seeded on 2 μm diameter Au sites and 200 nm diameter Au sites are illustrated in FIGS. 7A and 7B, respectively, along with their corresponding Fourier Transforms (FFT). The clusters are well defined and highly patterned with very little non-specific binding in the ITO interstitial areas. This is further confirmed by the well defined spots seen in the FFT, suggesting an ordered or patterned network. The cluster occupancy in the nano-patterned features in FIG. 4B is about 40-50% but can be increased further by using higher Avidin concentrations or by manipulating the voltage waveform. The same chemistry/process can be used to cluster with high spatial precision on dielectric sites as well. Ordered clusters on 700 nm diameter $SiO_2$ sites are shown in FIG. 8.

Mechanism

Figure 9A:
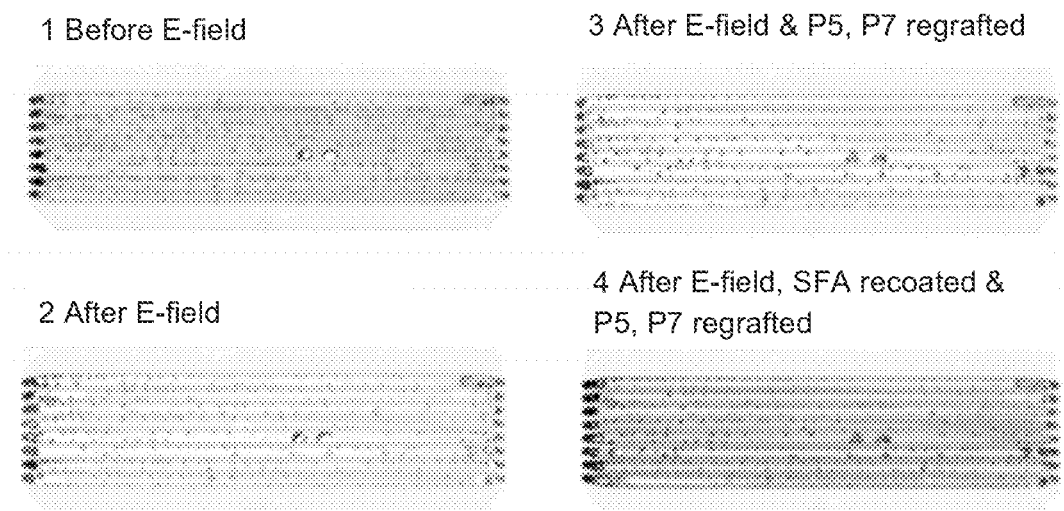
FIGS. 9A-9B show (FIG. 9A) results of a hybridization assay in a HiSeq flowcell (1) before electric field assisted P5 and P7 primer grafting, (2) after electric field assisted P5 and P7 primer grafting, (3) after electric field assisted P5 and P7 primer grafting and re-grafting P5 and P7 primers, and (4) after electric field assisted P5 and P7 primer grafting, SFA recoating and re-grafting P5 and P7 primers.
Figure 9B:
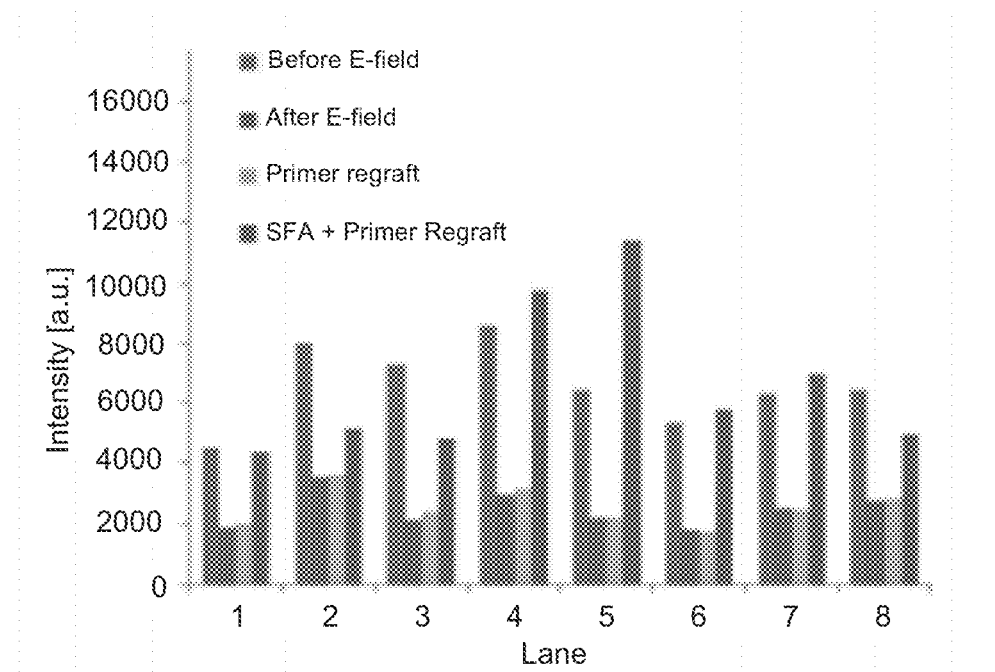

The data suggests that the spatial patterning of clusters is facilitated in the presence of an electric field. This is likely due to the electrochemical removal of biomolecules (e.g. DNA, proteins and primers) in the interstitial regions. Grafted primer intensity is seen to decrease when the electric field is applied as seen using hybridization assays with probes labeled with Texas Red (TR). FIGS. 9A-9B illustrate Typhoon scans showing TR fluorescence intensity for hybridization assays carried out in the flow cell before and after application of the electric field. Fluorescence intensity decreases by more than a factor of two after application of the electric field, confirming the removal of primers from the SFA. To increase the cluster intensity, the flow cell was re-coated with SFA and re-grafted with P5, P7 primers. This resulted in an appreciable increase in TR intensity. Thus, it is likely possible to seed DNA, electrochemically remove non-specifically bound molecules in interstitial regions, recoat SFA and re-graft primers to obtain high intensity, spatially patterned clusters.

Direct DNA Hybridization

Figure 10A:
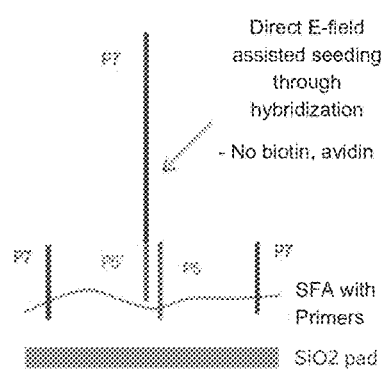
FIGS. 10A-10C shows (FIG. 10A) a schematic representation of direct hybridization on dielectric sites using electric field.
Figure 10B:
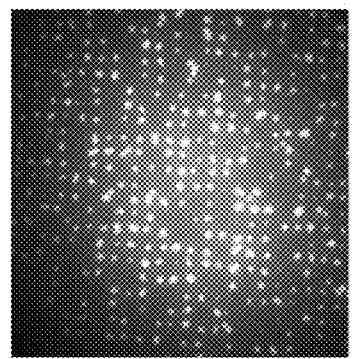
Figure 10C:
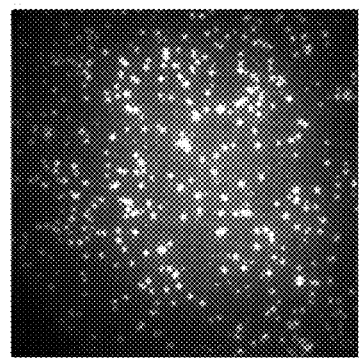

The spatial patterning of clusters was also observed in experiments involving the direct hybridization of phiX ssDNA to the P5, P7 primer lawn. A schematic of the process is shown in FIG. 10A. These experiments were conducted on 2 μm $SiO_2$ sites on ITO. The same process can be applied to nanopatterned sites with a variety of dielectric materials forming the sites. Neither biotinylated DNA, nor avidin are required in these experiments resulting in fewer chemistry steps, whilst maintaining cluster specificity on the sites. The specificity is likely the result of electrochemical desorption of primers in the interstitial regions. FIG. 10B shows clusters formed on 2 μm $SiO_2$ sites in the presence of an electric field (2V, 0.1 Hz) using the direct hybridization approach. Well patterned clusters are visible with very little in the interstitial regions. FIG. 10C is the same experiment in the absence of an electric field and shows that clusters are randomly oriented on both the SFA and the ITO interstitial regions with no distinct order present in the absence of the electric field. These results confirm that electric fields can be used to assist spatial patterning of nucleic acid cluster formation.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

The invention claimed is:

1. A method for amplifying nucleic acids, comprising
(a) providing
   (i) an array of amplification sites having one or more capture agents, and
   (ii) an amplification reagent comprising a solution comprising a plurality of different target nucleic acids,
   wherein the number of the different target nucleic acids in the solution exceeds the number of amplification sites in the array,
   wherein the different target nucleic acids have fluidic access to the plurality of amplification sites, and
   wherein each of the amplification sites is capable of being occupied by several target nucleic acids of the plurality of different target nucleic acids; and
(b) reacting the amplification reagent with the array of amplification sites, such that a plurality of amplification sites each comprises clonal amplicons from an individual target nucleic acid from the solution;
wherein the reacting comprises simultaneously
   (i) transporting the different target nucleic acids to the amplification sites to seed the different target nucleic acids at the amplification sites, and
   (ii) amplifying the target nucleic acids that are seeded at the amplification sites, where the amplification rate exceeds the seeding rate, such that the generated amplicons prevent additional target nucleic acids from being seeded at each of said plurality of amplification sites, and thereby prevents them from being amplified at each of said plurality of amplification sites.

2. The method of claim 1, wherein each of the amplification sites comprises a plurality of capture agents capable of binding to the different target nucleic acids in the solution.

3. The method of claim 1, wherein the array of amplification sites comprises an array of features on a surface.

4. The method of claim 3, wherein the area for each of the features is greater than the diameter of the excluded volume of the target nucleic acids that are transported to the amplification sites.

5. The method of claim 3, wherein the features are non-contiguous and are separated by interstitial regions of the surface that lack the capture agents.

6. The method of claim 3, wherein each of the features comprises a bead, well, channel, ridge, projection or combination thereof.

7. The method of claim 1, wherein the array of amplification sites comprises beads in solution or beads on a surface.

8. The method of claim 2, wherein the capture agents comprise capture nucleic acids that are complementary to the different target nucleic acids.

9. The method of claim 8, wherein the different target nucleic acids comprise universal sequences that are complementary to the capture nucleic acids.

10. The method of claim 1, wherein each of the amplification sites comprises a plurality of primers that are used to produce the amplicons in (b).

11. The method of claim 10, wherein the array of amplification sites comprises an array of features on a surface wherein the features are non-contiguous and are separated by interstitial regions of the surface that lack the primers that are used to produce the amplicons in (b).

12. The method of claim 1, wherein the amplification reagent further comprises recombinase and a single stranded binding protein, and/or a molecular crowding agent.

13. The method of claim 1, wherein the amplifying of the target nucleic acids that are transported to the amplification sites does not include a denaturation cycle.

14. The method of claim 1, wherein the plurality of amplification sites that comprise a clonal population of amplicons exceeds 40% of the amplification sites for which the different target nucleic acids had fluidic access.

15. The method of claim 1, wherein the different target nucleic acids are actively transported to the amplification sites assisted by application of an electric field.

16. The method of claim 15 where the electric field is increased as the reacting proceeds over time.

17. The method of claim 15 wherein the array of amplification sites comprises an array of non-contiguous features on a surface, the features being separated by interstitial regions of the surface.

18. The method of claim 17, wherein the area for each of the features is greater than the diameter of the excluded volume of the target nucleic acids that are transported to the amplification sites.

19. The method of claim 17, wherein the different target nucleic acids are actively repelled from the interstitial regions by application of a second electric field.

20. The method of claim 1, wherein the transporting comprises passive diffusion.

* * * * *